United States Patent
Davies et al.

(10) Patent No.: US 11,950,884 B2
(45) Date of Patent: Apr. 9, 2024

(54) DEVICES, SYSTEMS, AND METHODS FOR ASSESSING A VESSEL

(71) Applicants: PHILIPS IMAGE GUIDED THERAPY CORPORATION, San Diego, CA (US); MEDSOLVE LIMITED, London (GB); IMPERIAL COLLEGE OF SCIENCE, TECHNOLOGY AND MEDICINE, London (GB)

(72) Inventors: Justin Davies, London (GB); Joseph Burnett, Carlsbad, CA (US); Neil Hattangadi, San Diego, CA (US); David Anderson, Temecula, CA (US); Helen Davies, London (GB)

(73) Assignees: PHILIPS IMAGE GUIDED THERAPY CORPORATION, San Diego, CA (US); IMPERIAL COLLEGE OF SCIENCE, TECHNOLOGY & MEDICINE, London (GB); MEDSOLVE LIMITED, London (GB)

( * ) Notice: Subject to any disclaimer, the term of this patent is extended or adjusted under 35 U.S.C. 154(b) by 507 days.

(21) Appl. No.: 17/169,013

(22) Filed: Feb. 5, 2021

(65) Prior Publication Data

US 2021/0251496 A1    Aug. 19, 2021

Related U.S. Application Data

(63) Continuation of application No. 15/081,323, filed on Mar. 25, 2016, now Pat. No. 10,912,463, which is a
(Continued)

(51) Int. Cl.
*A61B 5/02*      (2006.01)
*A61B 5/00*      (2006.01)
(Continued)

(52) U.S. Cl.
CPC ........ *A61B 5/02007* (2013.01); *A61B 5/0215* (2013.01); *A61B 5/02158* (2013.01);
(Continued)

(58) Field of Classification Search
CPC ..... A61B 5/0215; A61B 5/6851; A61B 5/026; A61B 5/02158; A61B 5/6852;
(Continued)

(56) References Cited

U.S. PATENT DOCUMENTS

| 4,821,735 A | 4/1989 | Goor et al. |
| 5,775,338 A | 7/1998 | Hastings |

(Continued)

FOREIGN PATENT DOCUMENTS

| EP | 2298162 | 3/2011 |
| WO | WO 00/53081 A1 | 9/2000 |

(Continued)

OTHER PUBLICATIONS

SmartFlow™ Integrated Lumen Physiology, Version 5.0, Operator's Manual, Apr. 2001.
(Continued)

*Primary Examiner* — Carrie R Dorna
*Assistant Examiner* — Karen E Toth

(57) ABSTRACT

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries without the administration of a hyperemic agent.

13 Claims, 25 Drawing Sheets

Related U.S. Application Data continuation of application No. 13/460,296, filed on Apr. 30, 2012, now Pat. No. 9,339,348.

(60) Provisional application No. 61/525,736, filed on Aug. 20, 2011, provisional application No. 61/525,739, filed on Aug. 20, 2011.

(51) Int. Cl.
    *A61B 5/021*     (2006.01)
    *A61B 5/0215*     (2006.01)
    *A61B 5/026*     (2006.01)
    *A61B 34/10*     (2016.01)

(52) U.S. Cl.
CPC ............ *A61B 5/7203* (2013.01); *A61B 5/742* (2013.01); *A61B 34/10* (2016.02); *A61B 5/02* (2013.01); *A61B 5/021* (2013.01); *A61B 5/026* (2013.01); *A61B 5/6851* (2013.01); *A61B 5/6852* (2013.01); *A61B 5/743* (2013.01); *A61B 2562/0247* (2013.01)

(58) Field of Classification Search
CPC . A61B 5/743; A61B 5/021; A61B 2562/0247; A61B 5/02
See application file for complete search history.

(56) References Cited

U.S. PATENT DOCUMENTS

| | | | |
|---|---|---|---|
| 6,062,089 | A | 5/2000 | Ichihashi |
| 6,106,476 | A | 8/2000 | Corl et al. |
| 6,129,674 | A | 10/2000 | Ovadia-Blechman et al. |
| 6,190,355 | B1 | 2/2001 | Hastings |
| 6,193,669 | B1 | 2/2001 | Degany et al. |
| 6,296,615 | B1 | 10/2001 | Brockway et al. |
| 6,343,514 | B1 | 2/2002 | Smith |
| 6,354,999 | B1 | 3/2002 | Degany et al. |
| 6,409,677 | B1 | 6/2002 | Tulkki |
| 6,471,656 | B1* | 10/2002 | Shalman ............... A61B 5/6851 600/561 |
| 6,558,334 | B2 | 5/2003 | Shalman et al. |
| 6,565,514 | B2 | 5/2003 | Svanerudh et al. |
| 6,585,660 | B2 | 7/2003 | Dorando et al. |
| 6,616,667 | B1 | 9/2003 | Smith |
| 6,659,959 | B2 | 12/2003 | Brockway et al. |
| 6,663,570 | B2 | 12/2003 | Mott et al. |
| 6,697,667 | B1 | 2/2004 | Lee et al. |
| 6,716,178 | B1 | 4/2004 | Kilpatrick et al. |
| 6,754,608 | B2 | 6/2004 | Svanerudh et al. |
| 6,868,736 | B2 | 3/2005 | Sawatari et al. |
| 7,134,994 | B2 | 11/2006 | Alpert et al. |
| 7,274,956 | B2 | 9/2007 | Mott et al. |
| RE39,863 | E | 10/2007 | Smith |
| 7,329,223 | B1 | 2/2008 | Ainsworth et al. |
| 7,481,774 | B2 | 1/2009 | Brockway et al. |
| 7,532,920 | B1 | 5/2009 | Ainsworth et al. |
| 7,632,304 | B2 | 12/2009 | Park |
| 7,693,563 | B2 | 4/2010 | Suresh |
| 7,775,988 | B2 | 8/2010 | Pijls |
| 7,783,338 | B2 | 8/2010 | Ainsworth et al. |
| 7,814,635 | B2 | 10/2010 | Gordon et al. |
| 7,828,841 | B2 | 11/2010 | Mathis et al. |
| 7,828,842 | B2 | 11/2010 | Nieminen et al. |
| 7,828,843 | B2 | 11/2010 | Alferness et al. |
| 7,853,626 | B2 | 12/2010 | Jung et al. |
| 7,887,582 | B2 | 2/2011 | Mathis et al. |
| 8,006,594 | B2 | 8/2011 | Hayner et al. |
| 8,029,447 | B2 | 10/2011 | Kanz et al. |
| 8,062,358 | B2 | 11/2011 | Mathis et al. |
| 8,075,608 | B2 | 12/2011 | Gordon et al. |
| 8,157,742 | B2 | 4/2012 | Taylor |
| 2002/0016548 | A1* | 2/2002 | Stadler ............... A61B 5/7203 600/509 |
| 2002/0052553 | A1 | 5/2002 | Shalman et al. |
| 2002/0059827 | A1 | 5/2002 | Smith |
| 2002/0065472 | A1 | 5/2002 | Brockway et al. |
| 2002/0072880 | A1 | 6/2002 | Svanerudh et al. |
| 2002/0173724 | A1 | 11/2002 | Dorando et al. |
| 2003/0018273 | A1 | 1/2003 | Corl |
| 2003/0032886 | A1 | 2/2003 | Degany et al. |
| 2003/0033095 | A1 | 2/2003 | Svanerudh et al. |
| 2003/0159518 | A1 | 8/2003 | Sawatari et al. |
| 2003/0163052 | A1 | 8/2003 | Mott et al. |
| 2003/0191400 | A1 | 10/2003 | Shalman et al. |
| 2003/0195428 | A1 | 10/2003 | Brockway et al. |
| 2003/0204160 | A1 | 10/2003 | Kamm |
| 2003/0216621 | A1 | 11/2003 | Alpert et al. |
| 2004/0034294 | A1* | 2/2004 | Kimball ............... A61B 5/6826 600/323 |
| 2004/0082866 | A1 | 4/2004 | Mott et al. |
| 2004/0158321 | A1 | 8/2004 | Reuter et al. |
| 2005/0121734 | A1 | 6/2005 | Degertekin et al. |
| 2006/0041281 | A1* | 2/2006 | Von Arx ............... A61B 5/02108 607/18 |
| 2006/0052700 | A1 | 3/2006 | Svanerudh |
| 2006/0074318 | A1 | 4/2006 | Ahmed et al. |
| 2006/0106321 | A1 | 5/2006 | Lewinsky et al. |
| 2006/0241505 | A1 | 10/2006 | Ahmed et al. |
| 2007/0038129 | A1* | 2/2007 | Kishimoto ............ G16H 40/63 600/485 |
| 2007/0060822 | A1 | 3/2007 | Alpert et al. |
| 2007/0078352 | A1 | 4/2007 | Pijls |
| 2007/0225606 | A1 | 9/2007 | Naghavi et al. |
| 2007/0225614 | A1 | 9/2007 | Naghavi et al. |
| 2007/0255145 | A1 | 11/2007 | Smith et al. |
| 2007/0276264 | A1* | 11/2007 | Eide ................... A61B 5/03 600/485 |
| 2008/0027330 | A1 | 1/2008 | Naghavi et al. |
| 2008/0081957 | A1 | 4/2008 | Jung et al. |
| 2008/0082522 | A1 | 4/2008 | Jung et al. |
| 2008/0082582 | A1 | 4/2008 | Jung et al. |
| 2008/0101532 | A1 | 5/2008 | Tkaczyk |
| 2008/0139951 | A1 | 6/2008 | Patangay et al. |
| 2008/0213165 | A1 | 9/2008 | Lieu et al. |
| 2008/0228086 | A1 | 9/2008 | Johnson et al. |
| 2008/0242978 | A1* | 10/2008 | Simon ................. A61B 90/36 600/426 |
| 2008/0255466 | A1 | 10/2008 | Wellnhofer |
| 2008/0255471 | A1 | 10/2008 | Naghavi et al. |
| 2008/0269572 | A1 | 10/2008 | Kanz et al. |
| 2008/0281205 | A1 | 11/2008 | Naghavi et al. |
| 2008/0292049 | A1 | 11/2008 | Camus et al. |
| 2009/0005703 | A1* | 1/2009 | Fasciano ............... A61B 5/742 600/300 |
| 2009/0018408 | A1* | 1/2009 | Ouchi ................... A61B 5/681 600/509 |
| 2009/0018459 | A1 | 1/2009 | Tseng et al. |
| 2009/0081120 | A1 | 3/2009 | Lieu et al. |
| 2009/0082678 | A1 | 3/2009 | Smith |
| 2009/0088650 | A1 | 4/2009 | Corl et al. |
| 2009/0234231 | A1 | 9/2009 | Knight et al. |
| 2010/0081941 | A1 | 4/2010 | Naghavi et al. |
| 2010/0081943 | A1* | 4/2010 | Watson ................. A61B 5/4809 600/484 |
| 2010/0086483 | A1 | 4/2010 | Belardinelli et al. |
| 2010/0109104 | A1 | 5/2010 | Tiensuu et al. |
| 2010/0162807 | A1 | 6/2010 | Kassab |
| 2010/0210954 | A1 | 8/2010 | Bennett |
| 2010/0234698 | A1 | 9/2010 | Manstrom et al. |
| 2010/0241008 | A1 | 9/2010 | Belleville et al. |
| 2010/0280396 | A1 | 11/2010 | Zhang |
| 2010/0286537 | A1 | 11/2010 | Pijls |
| 2011/0066047 | A1 | 3/2011 | Belleville et al. |
| 2011/0071404 | A1 | 3/2011 | Schmitt et al. |
| 2011/0071407 | A1 | 3/2011 | Hubinette et al. |
| 2011/0085977 | A1 | 4/2011 | Rosenmeier |
| 2011/0087116 | A1* | 4/2011 | Parkin ................. G16H 20/17 600/485 |
| 2011/0137140 | A1 | 6/2011 | Tearney et al. |
| 2011/0137210 | A1 | 6/2011 | Johnson |
| 2011/0178383 | A1 | 7/2011 | Kassab |

(56) References Cited

U.S. PATENT DOCUMENTS

| | | | |
|---|---|---|---|
| 2011/0178413 | A1 | 7/2011 | Schmitt et al. |
| 2011/0178417 | A1 | 7/2011 | Kassab |
| 2011/0196255 | A1 | 8/2011 | Kassab |
| 2011/0245693 | A1 | 10/2011 | Hastings et al. |
| 2011/0251497 | A1 | 10/2011 | Corl et al. |
| 2011/0263986 | A1 | 10/2011 | Park et al. |
| 2011/0282216 | A1* | 11/2011 | Shinar ............... G16H 40/63 600/483 |
| 2011/0306867 | A1 | 12/2011 | Gopinathan et al. |
| 2011/0316704 | A1* | 12/2011 | Nielsen ............... G16H 15/00 702/187 |
| 2011/0319752 | A1 | 12/2011 | Steinberg et al. |
| 2011/0319773 | A1 | 12/2011 | Kanz et al. |
| 2012/0004529 | A1 | 1/2012 | Tolkowsky et al. |
| 2012/0004537 | A1 | 1/2012 | Tolkowsky et al. |
| 2012/0029339 | A1 | 2/2012 | Cohen et al. |
| 2012/0041318 | A1 | 2/2012 | Taylor |
| 2012/0041319 | A1 | 2/2012 | Taylor et al. |
| 2012/0041320 | A1 | 2/2012 | Taylor |
| 2012/0041321 | A1 | 2/2012 | Taylor |
| 2012/0041322 | A1 | 2/2012 | Taylor et al. |
| 2012/0041323 | A1 | 2/2012 | Taylor et al. |
| 2012/0041324 | A1 | 2/2012 | Taylor |
| 2012/0041735 | A1 | 2/2012 | Taylor |
| 2012/0041739 | A1 | 2/2012 | Taylor |
| 2012/0052918 | A1 | 3/2012 | Taylor |
| 2012/0053919 | A1 | 3/2012 | Taylor |
| 2012/0053921 | A1 | 3/2012 | Taylor |
| 2012/0059246 | A1 | 3/2012 | Taylor |
| 2012/0065514 | A1 | 3/2012 | Naghavi et al. |
| 2012/0065623 | A1 | 3/2012 | Nelson, III et al. |
| 2012/0071782 | A1 | 3/2012 | Patil et al. |
| 2012/0072190 | A1 | 3/2012 | Sharma et al. |
| 2012/0093266 | A1 | 4/2012 | Sun et al. |
| 2012/0101355 | A1 | 4/2012 | Gopinathan et al. |
| 2012/0101369 | A1 | 4/2012 | Patil et al. |
| 2012/0220883 | A1 | 8/2012 | Manstrom et al. |
| 2012/0319862 | A1* | 12/2012 | Nagy ............... H04Q 9/00 340/870.02 |
| 2013/0345574 | A1 | 12/2013 | Davies |
| 2018/0228387 | A1 | 8/2018 | Park |

FOREIGN PATENT DOCUMENTS

| | | | |
|---|---|---|---|
| WO | 2006041346 | A1 | 4/2006 |
| WO | 2012030882 | A1 | 3/2010 |
| WO | 2010103277 | A1 | 9/2010 |
| WO | 2011038044 | A1 | 3/2011 |
| WO | WO 01/13779 | A1 | 3/2011 |
| WO | 2012093260 | A1 | 7/2012 |
| WO | 2012093266 | A1 | 7/2012 |

OTHER PUBLICATIONS

Florence Medical Innovations in Vascular Technology Business Plan, May 2002.
Florence Medical SmartFlow, CFR/FFR Manual, Mar. 2002.
SmartFlow CFR/FFR, Innovations in Vascular Technology, Model 2000, 2002, 6 pages.
Florence Medical, Annual Letter to Shareholders, May 17, 2001, 1 page.
Florence Medical LTD, Company Profile, May 2001, 4 pages.
SmartFlow™ Integrated Lumen Physiology for the Cathlab, SmartFlow CFR/FFR, Model 2000, Version 5.0 CFR/FFR, 2001, 2 pages.
Florence Medical Center 510(k) Summary SmartFlow™, May 14, 2001, 6 pages.
Florence Medical Center 510(k) Summary SmartFlow™, Oct. 2, 2001, 5 pages.
Florence Medical, Inc. News Release, Florence Medical Introduces SmartFlow Multiple Lesion™ Device at American College of Cardiology Meeting, Mar. 14, 2002, 2 pages.
The Free Library by Farlex, Florence Medical Introduces SmartFlow Multiple Lesion Device at American College of Cardiology Meeting, Mar. 14, 2002, 3 pages.
Florence Medecal innovations in vascular technology PowerPoint presentation, 2002.
Shalman, E., et al., Pergamon, Numberical modeling of the flow in stenosed coronary artery. The relationship between main hemodynamic parameters, accepted Oct. 2, 2001.
Shalman, E., et al., Pergamon, Pressure-based simultaneous CFR and FFR measurements: understanding the physiology of a stenosed vessel, accepted Oct. 6, 2000.
Grubert, Luis, M.D., et al., Simultaneous Assessment of Coronary Flow Reserve and Fractional Flow Reserve with a Novel Pressure-Based Method, Journal of Interventional Cardiology vol. 13, No. 5, 2000.
Davies, Justin E., et al., Evidence of a Dominant Backward-Propagating "Suction" Wave Responsible for Diastolic Coronary Filling in Humans, Attenuated in Left VentricularHypertrophy, Heart Failure, International Centre for Circulatory Health, St. Mary's Hospital and Imperial College, Department of Bioengineering, Physiological Flow Unit, and the Department of Clinical Engineering, Royal Brompton Hospital, London, United Kingdom, accepted Jan. 23, 2006, pp. 1768-1778.
Young, D.F., et al., Pressure Drop Across Artificially Induced Stenoses in the Femoral Arteries of Dogs, Circulation Research, 1975; 36: 735-743.
The International Bureau of WIPO, Notification Concerning Submission, Obtention or Transmittal of Priority Document for International Application No. PCT/GB2012/050024, dated Feb. 16, 2012, 1 page.
European Patent Office, the International Searching Authority, Notification of Transmittal of the International Search Report and the Written Opinion of the International Searching Authority, or the Declaration for International Application No. PCT/GB2012/050024, dated Apr. 19, 2012, 16 pages.
International Search Report and Written Opinion received in Patent Cooperation Treaty Application No. PCT/US2012/061566, dated Mar. 29, 2013, 9 pages.
International Search Report and Written Opinion received in Patent Cooperation Treaty Application No. PCT/US2013/057647, dated Dec. 12, 2013, 11 pages.
Patent Cooperation Treaty, "International Preliminary Report on Patentability," for Application No. PCT/US2013/057647, dated Mar. 12, 2015, 8 pages.
European Patent Office, "European Search Report" for Application No. 12825326.7, (PCT/US2012051566), dated Mar. 16, 2015, 7 pages.
European Patent Office, "European Search Report" for Application No. 12825326.7, (PCT/US2012051570), dated Mar. 16, 2015, 8 pages.
European Patent Office Extended European Search Report for Application No. 16188188.3, dated Jan. 3, 2017, 10 pages.
Mynard, JP et al "Accurate Automatic Detection of End-Diastole from Left Ventricular Pressure using Peak Curvature", IEEE Transacations on Miomedical Engineering, Nov. 1, 2008, 7 pages.
Pijls et al The Crux of Maximum Hyperemia, The American College of Cardiology Foundation, vol. 4, No. 10, 2011, pp. 1093-1095.
Khashaba et al Intracoronary Versus Intravenous Adenosine-Induced Maximal Coronary Hyperemia for Fractional Flow Reserve Measurements, Clinical Medicine Insights: Cardiology, 2014, pp. 17-21.
Schlundt et al Comparison of Intracoronary Versus Intravenous Administration of Adenosine for Measurment of Coronary Fractional Flow Reserve, Circulation Cardiovascular Interv. American Heart Association, Inc. 2015, pp. 1-7.
Taylor, C.A. "Patient-Specific Modeling of Cardiobascular Mechanics", Annual Review of Biomedical Engineering, vol. 11, Apr. 2009, pp. 109-127.
Sen et al Development and Validation of a New Adenosine-Independent Index Stenosis Severity from Coronary Wave-Intensity Analysis, Journal of the American College of Cardiology, vol. 59, No. 15, 2012, pp. 1392-1402.

(56) References Cited

OTHER PUBLICATIONS

Khir, A.W. et al "Determination of Wave Speed and Wave Separation in the Arteries", Journal of Biomechanics, vol. 34, No. 9, Sep. 2001, pp. 1145-1155.
Jazmin Aguado-Sierra et al "Pressure Reservior-Wave Separation Applied to Coronary Arterial Data", 29th IEEE EMBS Annual International Conference, 2007.
Escaned, Javier et al "Importance of Diastolic Fractional Flow Reserve and Dobutamine challenge in Physiologic Assessment of Myocardial Bridging", Journal of the American College of Cardiology, vol. 42, Jul. 2003.
Abe, Masayuki et al "Diastolic Fractional Flow Reserve to Assess the Functional Severity of Moderate Coronary Artery Stenoses", Circulation, vol. 102, pp. 2365-2370, Nov. 2000.
Mamas, Mamas A. et al."Resting Pd/Pa Measured with Intracoronary Pressure Wire Strongly Predicts Fractional Flow Reserve", The Journal of Invasive Cardiology, vol. 22, pp. 260-265, May 2010.

\* cited by examiner

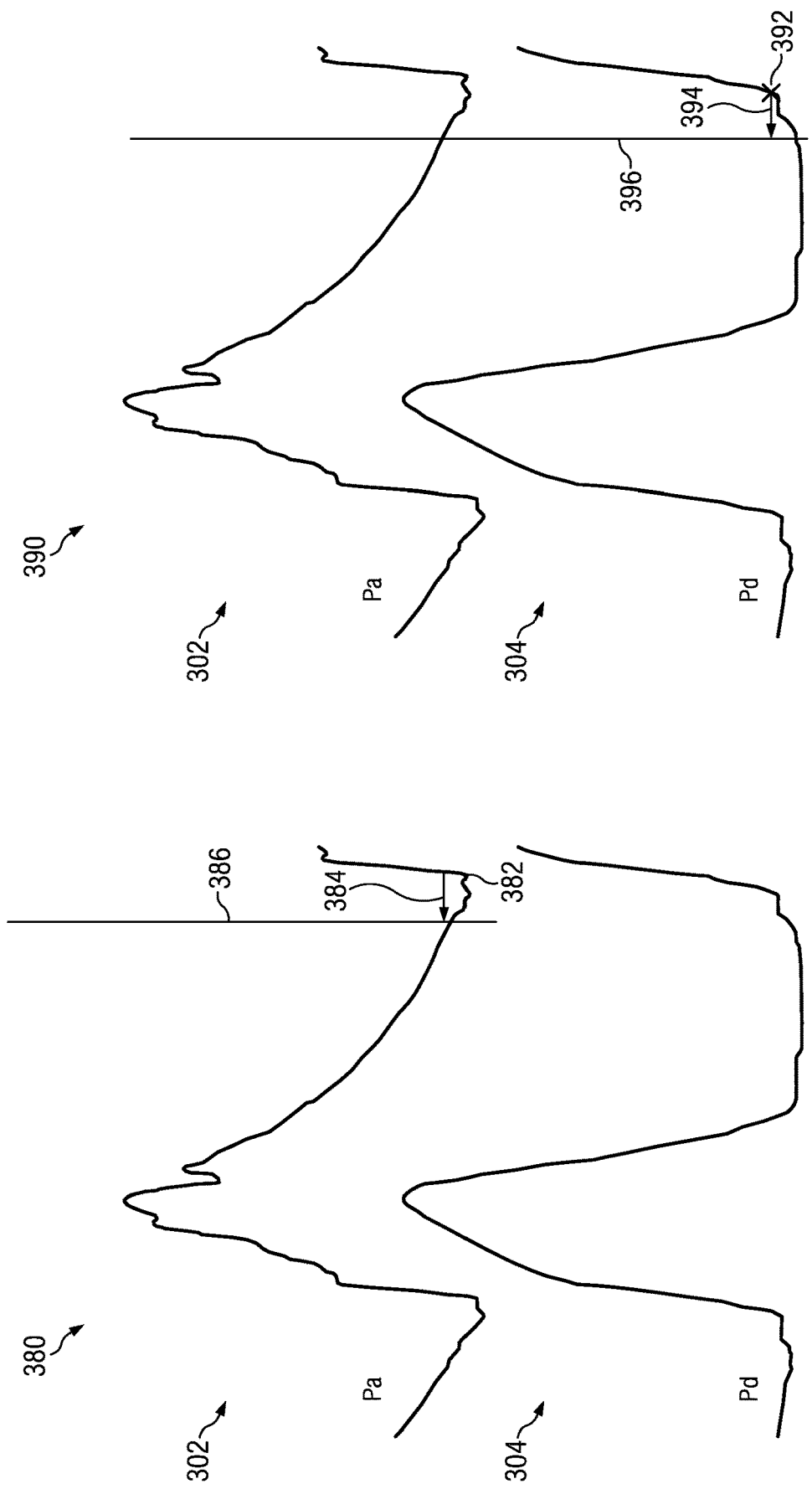

DEVICES, SYSTEMS, AND METHODS FOR ASSESSING A VESSEL

CROSS-REFERENCE TO RELATED APPLICATIONS

The present application is a continuation of U.S. patent application Ser. No. 15/081,323, filed Mar. 25, 2016, now U.S. Pat. No. 10,912,463, which is a continuation of U.S. patent application Ser. No. 13/460,296, filed Apr. 30, 2012, now U.S. Pat. No. 9,339,348, which claims priority to and the benefit of U.S. Provisional Patent Application No. 61/525,736, filed on Aug. 20, 2011, and U.S. Provisional Patent Application No. 61/525,739, filed on Aug. 20, 2011, each of which is hereby incorporated by reference in its entirety.

TECHNICAL FIELD

The present disclosure relates generally to the assessment of vessels and, in particular, the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment. Common treatment options include angioplasty and stenting.

Coronary blood flow is unique in that it is affected not only by fluctuations in the pressure arising proximally (as in the aorta) but is also simultaneously affected by fluctuations arising distally in the microcirculation. Accordingly, it is not possible to accurately assess the severity of a coronary stenosis by simply measuring the fall in mean or peak pressure across the stenosis because the distal coronary pressure is not purely a residual of the pressure transmitted from the aortic end of the vessel. As a result, for an effective calculation of FFR within the coronary arteries, it is necessary to reduce the vascular resistance within the vessel. Currently, pharmacological hyperemic agents, such as adenosine, are administered to reduce and stabilize the resistance within the coronary arteries. These potent vasodilator agents reduce the dramatic fluctuation in resistance (predominantly by reducing the microcirculation resistance associated with the systolic portion of the heart cycle) to obtain a relatively stable and minimal resistance value.

However, the administration of hyperemic agents is not always possible or advisable. First, the clinical effort of administering hyperemic agents can be significant. In some countries (particularly the United States), hyperemic agents such as adenosine are expensive, and time consuming to obtain when delivered intravenously (IV). In that regard, IV-delivered adenosine is generally mixed on a case-by-case basis in the hospital pharmacy. It can take a significant amount of time and effort to get the adenosine prepared and delivered to the operating area. These logistic hurdles can impact a physician's decision to use FFR. Second, some patients have contraindications to the use of hyperemic agents such as asthma, severe COPD, hypotension, bradycardia, low cardiac ejection fraction, recent myocardial infarction, and/or other factors that prevent the administration of hyperemic agents. Third, many patients find the administration of hyperemic agents to be uncomfortable, which is only compounded by the fact that the hyperemic agent may need to be applied multiple times during the course of a procedure to obtain FFR measurements. Fourth, the administration of a hyperemic agent may also require central venous access (e.g., a central venous sheath) that might otherwise be avoided. Finally, not all patients respond as expected to hyperemic agents and, in some instances, it is difficult to identify these patients before administration of the hyperemic agent.

Accordingly, there remains a need for improved devices, systems, and methods for assessing the severity of a blockage in a vessel and, in particular, a stenosis in a blood vessel. In that regard, there remains a need for improved devices, systems, and methods for assessing the severity of a stenosis in the coronary arteries that do not require the administration of hyperemic agents.

SUMMARY

Embodiments of the present disclosure are configured to assess the severity of a blockage in a vessel and, in particular, a stenosis in a blood vessel. In some particular embodiments, the devices, systems, and methods of the present disclosure are configured to assess the severity of a stenosis in the coronary arteries without the administration of a hyperemic agent.

In some instances, a method of evaluating a vessel of a patient is provided. The method includes introducing at least one instrument into the vessel of the patient; obtaining from the at least one instrument proximal pressure measurements within the vessel at a position proximal of a stenosis of the vessel for at least one cardiac cycle of the patient; obtaining from the at least one instrument distal pressure measurements within the vessel at a position distal of the stenosis of the vessel for the at least one cardiac cycle of the patient; selecting a diagnostic window within a cardiac cycle of the patient, wherein the diagnostic window encompassing only a portion of the cardiac cycle of the patient; and calculating a pressure ratio between the distal pressure measurements obtained during the diagnostic window and the proximal pressure measurements obtained during the diagnostic window. In some embodiments, the diagnostic window is selected at least partially based on one or more characteristics of the proximal pressure measurements. For example, a starting point and/or an ending point of the diagnostic window is selected based on the proximal pressure measurements. In that regard, the starting and/or ending point is based on one or more of a dicrotic notch in the proximal pressure measurements, a peak pressure of the proximal pressure measurements, a maximum change in pressure of the proximal pressure measurements, a start of a cardiac cycle of the proximal pressure measurements, and a start of diastole of the proximal pressure measurements. In some instances, an ending point of the diagnostic window is selected to be a fixed amount of time from the starting point.

In some embodiments, the diagnostic window is selected at least partially based on one or more characteristics of the distal pressure measurements. For example, a starting point and/or an ending point of the diagnostic window is selected based on the distal pressure measurements. In that regard, the starting and/or ending point is based on one or more of a dicrotic notch in the distal pressure measurements, a peak pressure of the distal pressure measurements, a maximum change in pressure of the distal pressure measurements, a start of a cardiac cycle of the distal pressure measurements, a ventricularization point of the distal pressure measurements, and a start of diastole of the distal pressure measurements. In some instances, the diagnostic window is selected by identifying a maximum diagnostic window and selecting a portion of the maximum diagnostic window as the diagnostic window. Further, in some embodiments, the method further comprises obtaining from the at least one instrument flow velocity measurements of a fluid flowing through the vessel. In that regard, the diagnostic window is selected, in some instances, to correspond to a portion of the cardiac cycle where a differential, first derivative, and/or second derivative of the flow velocity measurements has a relatively constant value of approximately zero. In some embodiments, the diagnostic window is selected based on characteristics of an ECG signal of the patient. In some embodiments, the heart of the patient is not stressed during the at least one cardiac cycle in which the proximal and distal pressure measurements are taken. Further, in some embodiments, the method further comprises temporally aligning at least a portion of the proximal pressure measurements with at least a portion of the distal pressure measurements.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 24 is a graphical representation of an identification of an ending point of a diagnostic window based on a proximal pressure measurement according to an embodiment of the present disclosure.

FIG. 25 is a graphical representation of an identification of an ending point of a diagnostic window based on a distal pressure measurement according to an embodiment of the present disclosure.

DETAILED DESCRIPTION

Figure 1:
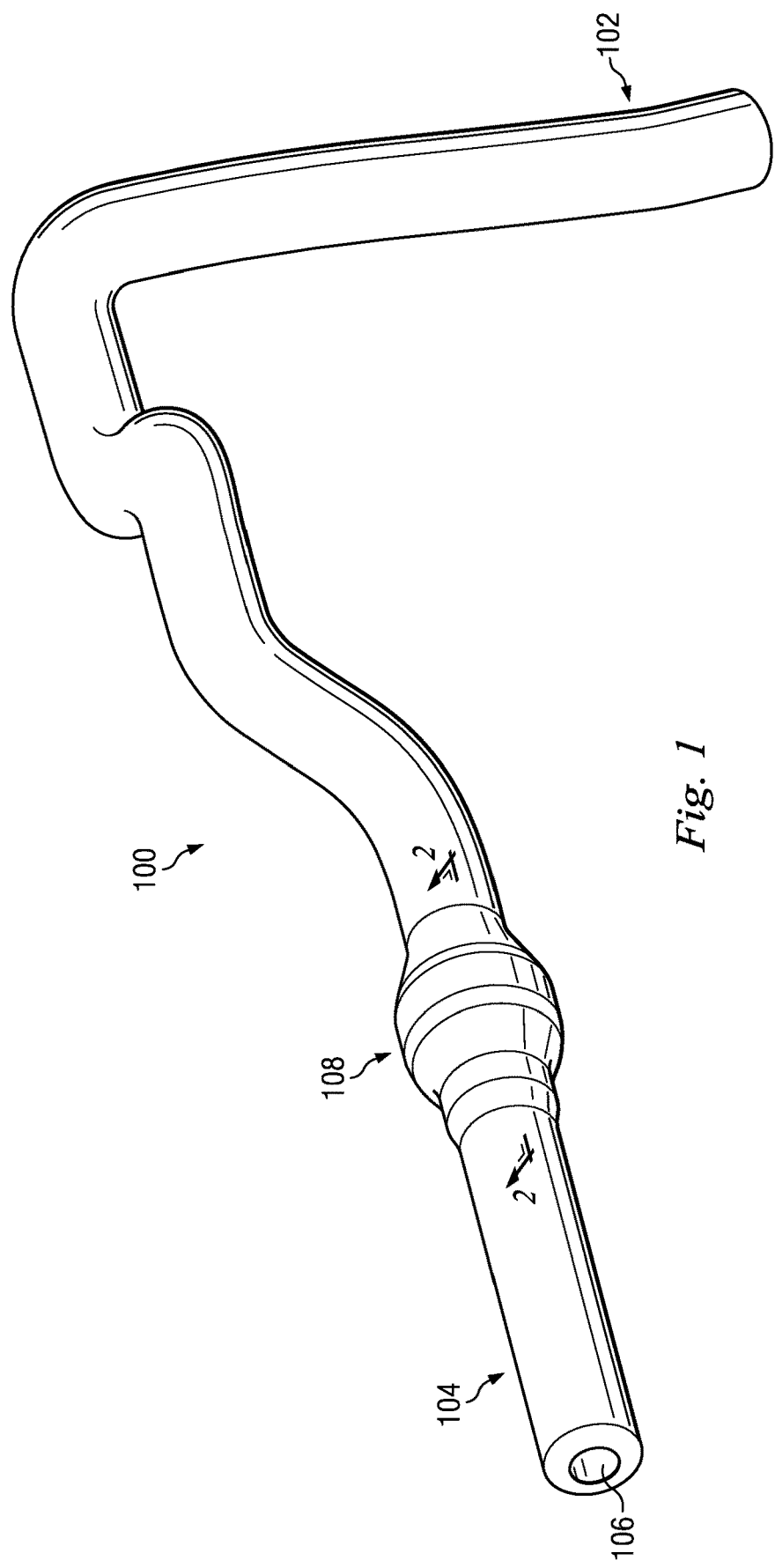
FIG. 1 is a diagrammatic perspective view of a vessel having a stenosis according to an embodiment of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 2:
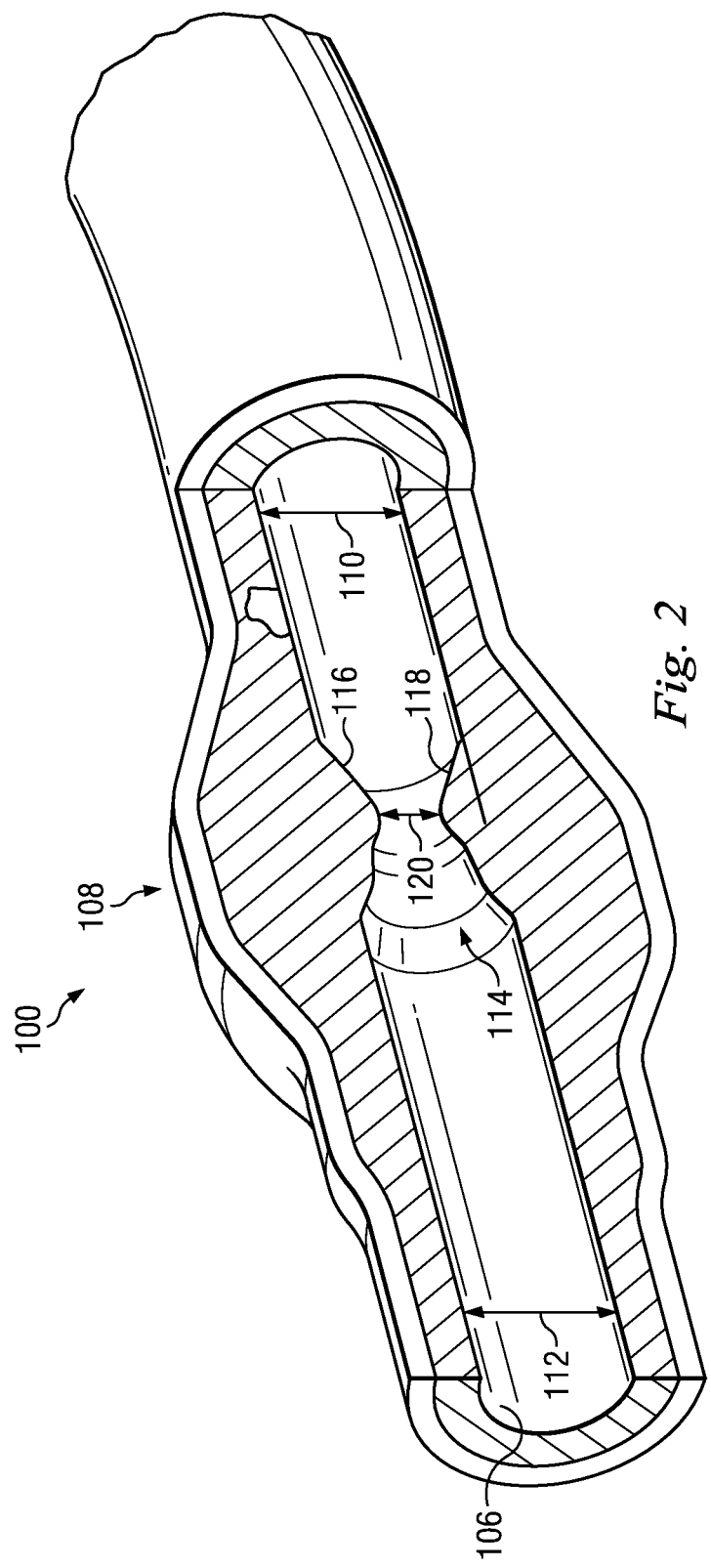
FIG. 2 is a diagrammatic, partial cross-sectional perspective view of a portion of the vessel of FIG. 1 taken along section line 2-2 of FIG. 1.

Referring to FIGS. 1 and 2, shown therein is a vessel 100 having a stenosis according to an embodiment of the present disclosure. In that regard, FIG. 1 is a diagrammatic perspective view of the vessel 100, while FIG. 2 is a partial cross-sectional perspective view of a portion of the vessel 100 taken along section line 2-2 of FIG. 1. Referring more specifically to FIG. 1, the vessel 100 includes a proximal portion 102 and a distal portion 104. A lumen 106 extends along the length of the vessel 100 between the proximal portion 102 and the distal portion 104. In that regard, the lumen 106 is configured to allow the flow of fluid through the vessel. In some instances, the vessel 100 is a systemic blood vessel. In some particular instances, the vessel 100 is a coronary artery. In such instances, the lumen 106 is configured to facilitate the flow of blood through the vessel 100.

As shown, the vessel 100 includes a stenosis 108 between the proximal portion 102 and the distal portion 104. Stenosis 108 is generally representative of any blockage or other structural arrangement that results in a restriction to the flow of fluid through the lumen 106 of the vessel 100. Embodiments of the present disclosure are suitable for use in a wide variety of vascular applications, including without limitation coronary, peripheral (including but not limited to lower limb, carotid, and neurovascular), renal, and/or venous. Where the vessel 100 is a blood vessel, the stenosis 108 may be a result of plaque buildup, including without limitation plaque components such as fibrous, fibro-lipidic (fibro fatty), necrotic core, calcified (dense calcium), blood, fresh thrombus, and mature thrombus. Generally, the composition of the stenosis will depend on the type of vessel being evaluated. In that regard, it is understood that the concepts of the present disclosure are applicable to virtually any type of blockage or other narrowing of a vessel that results in decreased fluid flow.

Referring more particularly to FIG. 2, the lumen 106 of the vessel 100 has a diameter 110 proximal of the stenosis 108 and a diameter 112 distal of the stenosis. In some instances, the diameters 110 and 112 are substantially equal to one another. In that regard, the diameters 110 and 112 are intended to represent healthy portions, or at least healthier portions, of the lumen 106 in comparison to stenosis 108. Accordingly, these healthier portions of the lumen 106 are illustrated as having a substantially constant cylindrical profile and, as a result, the height or width of the lumen has been referred to as a diameter. However, it is understood that in many instances these portions of the lumen 106 will also have plaque buildup, a non-symmetric profile, and/or other irregularities, but to a lesser extent than stenosis 108 and, therefore, will not have a cylindrical profile. In such instances, the diameters 110 and 112 are understood to be representative of a relative size or cross-sectional area of the lumen and do not imply a circular cross-sectional profile.

As shown in FIG. 2, stenosis 108 includes plaque buildup 114 that narrows the lumen 106 of the vessel 100. In some instances, the plaque buildup 114 does not have a uniform or symmetrical profile, making angiographic evaluation of such a stenosis unreliable. In the illustrated embodiment, the plaque buildup 114 includes an upper portion 116 and an opposing lower portion 118. In that regard, the lower portion 118 has an increased thickness relative to the upper portion 116 that results in a non-symmetrical and non-uniform profile relative to the portions of the lumen proximal and distal of the stenosis 108. As shown, the plaque buildup 114 decreases the available space for fluid to flow through the lumen 106. In particular, the cross-sectional area of the lumen 106 is decreased by the plaque buildup 114. At the narrowest point between the upper and lower portions 116, 118 the lumen 106 has a height 120, which is representative of a reduced size or cross-sectional area relative to the diameters 110 and 112 proximal and distal of the stenosis 108. Note that the stenosis 108, including plaque buildup 114 is exemplary in nature and should be considered limiting in any way. In that regard, it is understood that the stenosis 108 has other shapes and/or compositions that limit the flow of fluid through the lumen 106 in other instances. While the vessel 100 is illustrated in FIGS. 1 and 2 as having a single stenosis 108 and the description of the embodiments below is primarily made in the context of a single stenosis, it is nevertheless understood that the devices, systems, and methods described herein have similar application for a vessel having multiple stenosis regions.

Figure 3:
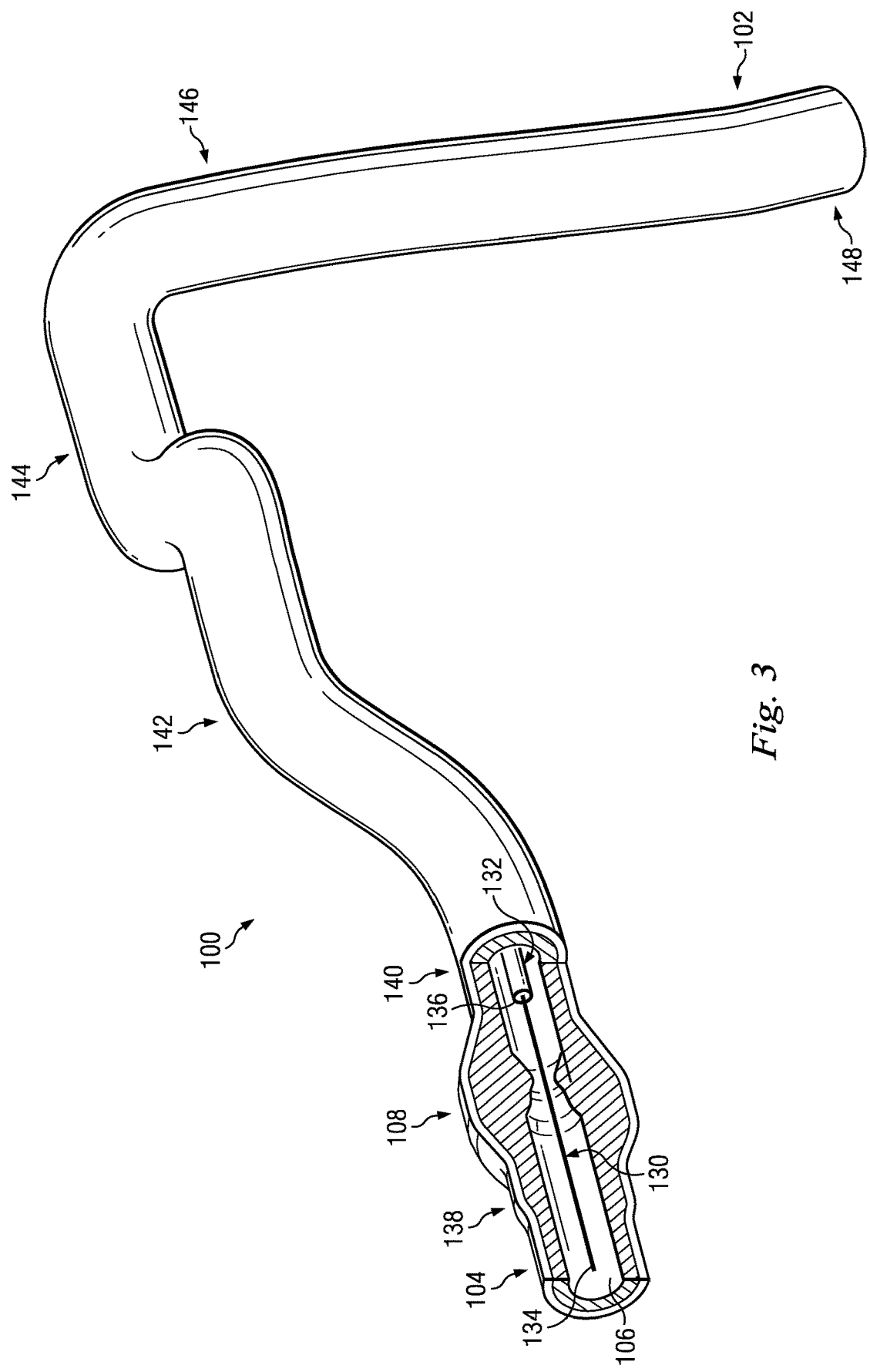
FIG. 3 is a diagrammatic, partial cross-sectional perspective view of the vessel of FIGS. 1 and 2 with instruments positioned therein according to an embodiment of the present disclosure.

Referring now to FIG. 3, the vessel 100 is shown with instruments 130 and 132 positioned therein according to an embodiment of the present disclosure. In general, instruments 130 and 132 may be any form of device, instrument, or probe sized and shaped to be positioned within a vessel. In the illustrated embodiment, instrument 130 is generally representative of a guide wire, while instrument 132 is generally representative of a catheter. In that regard, instrument 130 extends through a central lumen of instrument 132. However, in other embodiments, the instruments 130 and 132 take other forms. In that regard, the instruments 130 and 132 are of similar form in some embodiments. For example, in some instances, both instruments 130 and 132 are guide wires. In other instances, both instruments 130 and 132 are catheters. On the other hand, the instruments 130 and 132 are of different form in some embodiments, such as the illustrated embodiment, where one of the instruments is a catheter and the other is a guide wire. Further, in some instances, the instruments 130 and 132 are disposed coaxial with one another, as shown in the illustrated embodiment of FIG. 3. In other instances, one of the instruments extends through an off-center lumen of the other instrument. In yet other instances, the instruments 130 and 132 extend side-by-side. In some particular embodiments, at least one of the instruments is as a rapid-exchange device, such as a rapid-exchange catheter. In such embodiments, the other instrument is a buddy wire or other device configured to facilitate the introduction and removal of the rapid-exchange device. Further still, in other instances, instead of two separate instruments 130 and 132 a single instrument is utilized. In that regard, the single instrument incorporates aspects of the functionalities (e.g., data acquisition) of both instruments 130 and 132 in some embodiments.

Instrument 130 is configured to obtain diagnostic information about the vessel 100. In that regard, the instrument 130 includes one or more sensors, transducers, and/or other monitoring elements configured to obtain the diagnostic information about the vessel. The diagnostic information includes one or more of pressure, flow (velocity), images (including images obtained using ultrasound (e.g., IVUS), OCT, thermal, and/or other imaging techniques), temperature, and/or combinations thereof. The one or more sensors, transducers, and/or other monitoring elements are positioned adjacent a distal portion of the instrument 130 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 134 of the instrument 130 in some instances. In some instances, at least one of the one or more sensors, transducers, and/or other monitoring elements is positioned at the distal tip of the instrument 130.

The instrument 130 includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Examples of commercially available guide wire products that include suitable pressure monitoring elements include, without limitation, the PrimeWire PRESTIGE® pressure guide wire, the PrimeWire® pressure guide wire, and the ComboWire® XT pressure and flow guide wire, each available from Volcano Corporation, as well as the PressureWire' Certus guide wire and the PressureWire' Aeris guide wire, each available from St. Jude Medical, Inc. Generally, the instrument 130 is sized such that it can be positioned through the stenosis 108 without significantly impacting fluid flow across the stenosis, which would impact the distal pressure reading. Accordingly, in some instances the instrument 130 has an outer diameter of or less. In some embodiments, the instrument 130 has an outer diameter of 0.014" or less.

Instrument 132 is also configured to obtain diagnostic information about the vessel 100. In some instances, instrument 132 is configured to obtain the same diagnostic information as instrument 130. In other instances, instrument 132 is configured to obtain different diagnostic information than instrument 130, which may include additional diagnostic information, less diagnostic information, and/or alternative diagnostic information. The diagnostic information obtained by instrument 132 includes one or more of pressure, flow (velocity), images (including images obtained using ultrasound (e.g., IVUS), OCT, thermal, and/or other imaging techniques), temperature, and/or combinations thereof. Instrument 132 includes one or more sensors, transducers, and/or other monitoring elements configured to obtain this diagnostic information. In that regard, the one or more sensors, transducers, and/or other monitoring elements are positioned adjacent a distal portion of the instrument 132 in some instances. In that regard, the one or more sensors, transducers, and/or other monitoring elements are positioned less than 30 cm, less than 10 cm, less than 5 cm, less than 3 cm, less than 2 cm, and/or less than 1 cm from a distal tip 136 of the instrument 132 in some instances. In some instances, at least one of the one or more sensors, transducers, and/or other monitoring elements is positioned at the distal tip of the instrument 132.

Similar to instrument 130, instrument 132 also includes at least one element configured to monitor pressure within the vessel 100. The pressure monitoring element can take the form a piezo-resistive pressure sensor, a piezo-electric pressure sensor, a capacitive pressure sensor, an electromagnetic pressure sensor, a fluid column (the fluid column being in communication with a fluid column sensor that is separate from the instrument and/or positioned at a portion of the instrument proximal of the fluid column), an optical pressure sensor, and/or combinations thereof. In some instances, one or more features of the pressure monitoring element are implemented as a solid-state component manufactured using semiconductor and/or other suitable manufacturing techniques. Millar catheters are utilized in some embodiments. Currently available catheter products suitable for use with one or more of Philips's Xper Flex Cardio Physiomonitoring System, GE's Mac-Lab XT and XTi hemodynamic recording systems, Siemens's AXIOM Sensis XP VC11, McKesson's Horizon Cardiology Hemo, and Mennen's Horizon XVu Hemodynamic Monitoring System and include pressure monitoring elements can be utilized for instrument 132 in some instances.

In accordance with aspects of the present disclosure, at least one of the instruments 130 and 132 is configured to monitor a pressure within the vessel 100 distal of the stenosis 108 and at least one of the instruments 130 and 132 is configured to monitor a pressure within the vessel proximal of the stenosis. In that regard, the instruments 130, 132 are sized and shaped to allow positioning of the at least one element configured to monitor pressure within the vessel 100 to be positioned proximal and/or distal of the stenosis 108 as necessary based on the configuration of the devices. In that regard, FIG. 3 illustrates a position 138 suitable for measuring pressure distal of the stenosis 108. In that regard, the position 138 is less than 5 cm, less than 3 cm, less than 2 cm, less than 1 cm, less than 5 mm, and/or less than 2.5 mm from the distal end of the stenosis 108 (as shown in FIG. 2) in some instances. FIG. 3 also illustrates a plurality of suitable positions for measuring pressure proximal of the stenosis 108. In that regard, positions 140, 142, 144, 146, and 148 each represent a position that is suitable for monitoring the pressure proximal of the stenosis in some instances. In that regard, the positions 140, 142, 144, 146, and 148 are positioned at varying distances from the proximal end of the stenosis 108 ranging from more than 20 cm down to about 5 mm or less. Generally, the proximal pressure measurement will be spaced from the proximal end of the stenosis. Accordingly, in some instances, the proximal pressure measurement is taken at a distance equal to or greater than an inner diameter of the lumen of the vessel from the proximal end of the stenosis. In the context of coronary artery pressure measurements, the proximal pressure measurement is generally taken at a position proximal of the stenosis and distal of the aorta, within a proximal portion of the vessel. However, in some particular instances of coronary artery pressure measurements, the proximal pressure measurement is taken from a location inside the aorta. In other instances, the proximal pressure measurement is taken at the root or ostium of the coronary artery.

Figure 4:
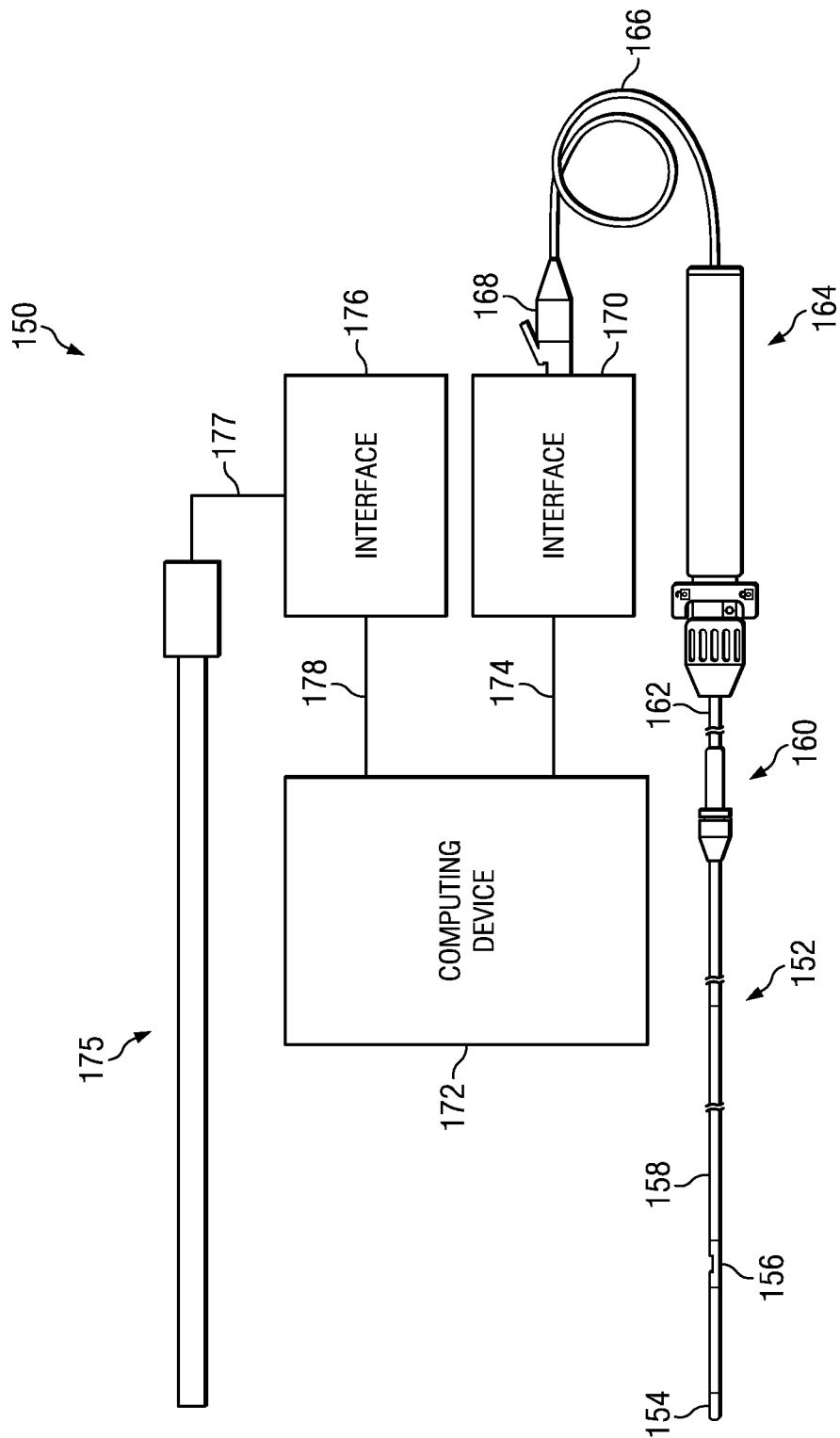
FIG. 4 is a diagrammatic, schematic view of a system according to an embodiment of the present disclosure.

Referring now to FIG. 4, shown therein is a system 150 according to an embodiment of the present disclosure. In that regard, FIG. 4 is a diagrammatic, schematic view of the system 150. As shown, the system 150 includes an instrument 152. In that regard, in some instances instrument 152 is suitable for use as at least one of instruments 130 and 132 discussed above. Accordingly, in some instances the instrument 152 includes features similar to those discussed above with respect to instruments 130 and 132 in some instances. In the illustrated embodiment, the instrument 152 is a guide wire having a distal portion 154 and a housing 156 positioned adjacent the distal portion. In that regard, the housing 156 is spaced approximately 3 cm from a distal tip of the instrument 152. The housing 156 is configured to house one or more sensors, transducers, and/or other monitoring elements configured to obtain the diagnostic information about the vessel. In the illustrated embodiment, the housing 156 contains at least a pressure sensor configured to monitor a pressure within a lumen in which the instrument 152 is positioned. A shaft 158 extends proximally from the housing 156. A torque device 160 is positioned over and coupled to a proximal portion of the shaft 158. A proximal end portion 162 of the instrument 152 is coupled to a connector 164. A cable 166 extends from connector 164 to a connector 168. In some instances, connector 168 is configured to be plugged into an interface 170. In that regard, interface 170 is a patient interface module (PIM) in some instances. In some instances, the cable 166 is replaced with a wireless connection. In that regard, it is understood that various communication pathways between the instrument 152 and the interface 170 may be utilized, including physical connections (including electrical, optical, and/or fluid connections), wireless connections, and/or combinations thereof.

The interface 170 is communicatively coupled to a computing device 172 via a connection 174. Computing device 172 is generally representative of any device suitable for performing the processing and analysis techniques discussed within the present disclosure. In some embodiments, the computing device 172 includes a processor, random access memory, and a storage medium. In that regard, in some particular instances the computing device 172 is programmed to execute steps associated with the data acquisition and analysis described herein. Accordingly, it is understood that any steps related to data acquisition, data processing, instrument control, and/or other processing or control aspects of the present disclosure may be implemented by the computing device using corresponding instructions stored on or in a non-transitory computer readable medium accessible by the computing device. In some instances, the computing device 172 is a console device. In some particular instances, the computing device 172 is similar to the s5™ Imaging System or the s5i™ Imaging System, each available from Volcano Corporation. In some instances, the computing device 172 is portable (e.g., handheld, on a rolling cart, etc.). Further, it is understood that in some instances the computing device 172 comprises a plurality of computing devices. In that regard, it is particularly understood that the different processing and/or control aspects of the present disclosure may be implemented separately or within predefined groupings using a plurality of computing devices. Any divisions and/or combinations of the processing and/or control aspects described below across multiple computing devices are within the scope of the present disclosure.

Together, connector 164, cable 166, connector 168, interface 170, and connection 174 facilitate communication between the one or more sensors, transducers, and/or other monitoring elements of the instrument 152 and the computing device 172. However, this communication pathway is exemplary in nature and should not be considered limiting in any way. In that regard, it is understood that any communication pathway between the instrument 152 and the computing device 172 may be utilized, including physical connections (including electrical, optical, and/or fluid connections), wireless connections, and/or combinations thereof. In that regard, it is understood that the connection 174 is wireless in some instances. In some instances, the connection 174 includes a communication link over a network (e.g., intranet, internet, telecommunications network, and/or other network). In that regard, it is understood that the computing device 172 is positioned remote from an operating area where the instrument 152 is being used in some instances. Having the connection 174 include a connection over a network can facilitate communication between the instrument 152 and the remote computing device 172 regardless of whether the computing device is in an adjacent room, an adjacent building, or in a different state/country. Further, it is understood that the communication pathway between the instrument 152 and the computing device 172 is a secure connection in some instances. Further still, it is understood that, in some instances, the data communicated over one or more portions of the communication pathway between the instrument 152 and the computing device 172 is encrypted.

The system 150 also includes an instrument 175. In that regard, in some instances instrument 175 is suitable for use as at least one of instruments 130 and 132 discussed above.

Accordingly, in some instances the instrument 175 includes features similar to those discussed above with respect to instruments 130 and 132 in some instances. In the illustrated embodiment, the instrument 175 is a catheter-type device. In that regard, the instrument 175 includes one or more sensors, transducers, and/or other monitoring elements adjacent a distal portion of the instrument configured to obtain the diagnostic information about the vessel. In the illustrated embodiment, the instrument 175 includes a pressure sensor configured to monitor a pressure within a lumen in which the instrument 175 is positioned. The instrument 175 is in communication with an interface 176 via connection 177. In some instances, interface 176 is a hemodynamic monitoring system or other control device, such as Siemens AXIOM Sensis, Mennen Horizon XVu, and Philips Xper IM Physiomonitoring 5. In one particular embodiment, instrument 175 is a pressure-sensing catheter that includes fluid column extending along its length. In such an embodiment, interface 176 includes a hemostasis valve fluidly coupled to the fluid column of the catheter, a manifold fluidly coupled to the hemostasis valve, and tubing extending between the components as necessary to fluidly couple the components. In that regard, the fluid column of the catheter is in fluid communication with a pressure sensor via the valve, manifold, and tubing. In some instances, the pressure sensor is part of interface 176. In other instances, the pressure sensor is a separate component positioned between the instrument 175 and the interface 176. The interface 176 is communicatively coupled to the computing device 172 via a connection 178.

Similar to the connections between instrument 152 and the computing device 172, interface 176 and connections 177 and 178 facilitate communication between the one or more sensors, transducers, and/or other monitoring elements of the instrument 175 and the computing device 172. However, this communication pathway is exemplary in nature and should not be considered limiting in any way. In that regard, it is understood that any communication pathway between the instrument 175 and the computing device 172 may be utilized, including physical connections (including electrical, optical, and/or fluid connections), wireless connections, and/or combinations thereof. In that regard, it is understood that the connection 178 is wireless in some instances. In some instances, the connection 178 includes a communication link over a network (e.g., intranet, internet, telecommunications network, and/or other network). In that regard, it is understood that the computing device 172 is positioned remote from an operating area where the instrument 175 is being used in some instances. Having the connection 178 include a connection over a network can facilitate communication between the instrument 175 and the remote computing device 172 regardless of whether the computing device is in an adjacent room, an adjacent building, or in a different state/country. Further, it is understood that the communication pathway between the instrument 175 and the computing device 172 is a secure connection in some instances. Further still, it is understood that, in some instances, the data communicated over one or more portions of the communication pathway between the instrument 175 and the computing device 172 is encrypted.

It is understood that one or more components of the system 150 are not included, are implemented in a different arrangement/order, and/or are replaced with an alternative device/mechanism in other embodiments of the present disclosure. For example, in some instances, the system 150 does not include interface 170 and/or interface 176. In such instances, the connector 168 (or other similar connector in communication with instrument 152 or instrument 175) may plug into a port associated with computing device 172. Alternatively, the instruments 152, 175 may communicate wirelessly with the computing device 172. Generally speaking, the communication pathway between either or both of the instruments 152, 175 and the computing device 172 may have no intermediate nodes (i.e., a direct connection), one intermediate node between the instrument and the computing device, or a plurality of intermediate nodes between the instrument and the computing device.

Figure 5:
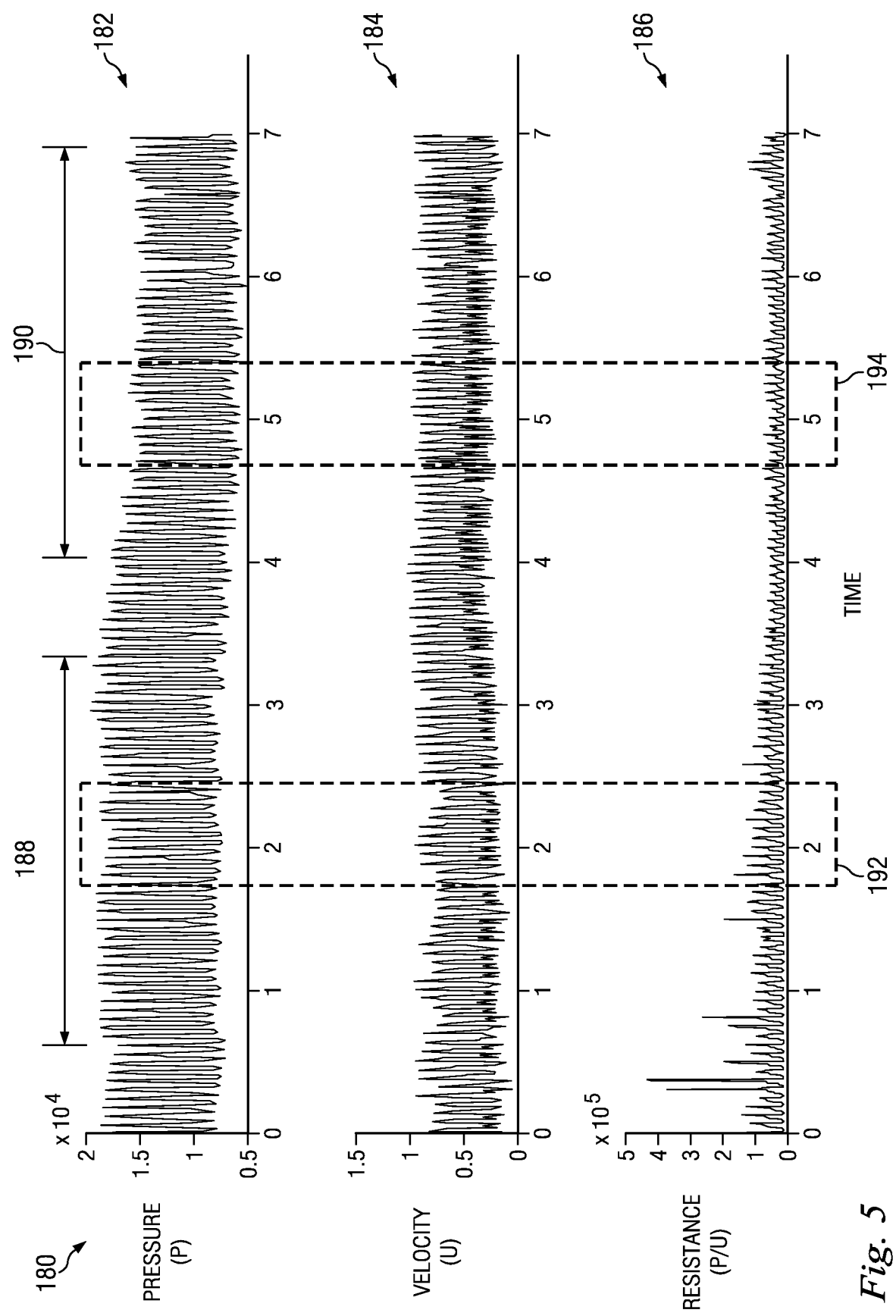
FIG. 5 is a graphical representation of measured pressure, velocity, and resistance within a vessel according to an embodiment of the present disclosure.
Figure 6:
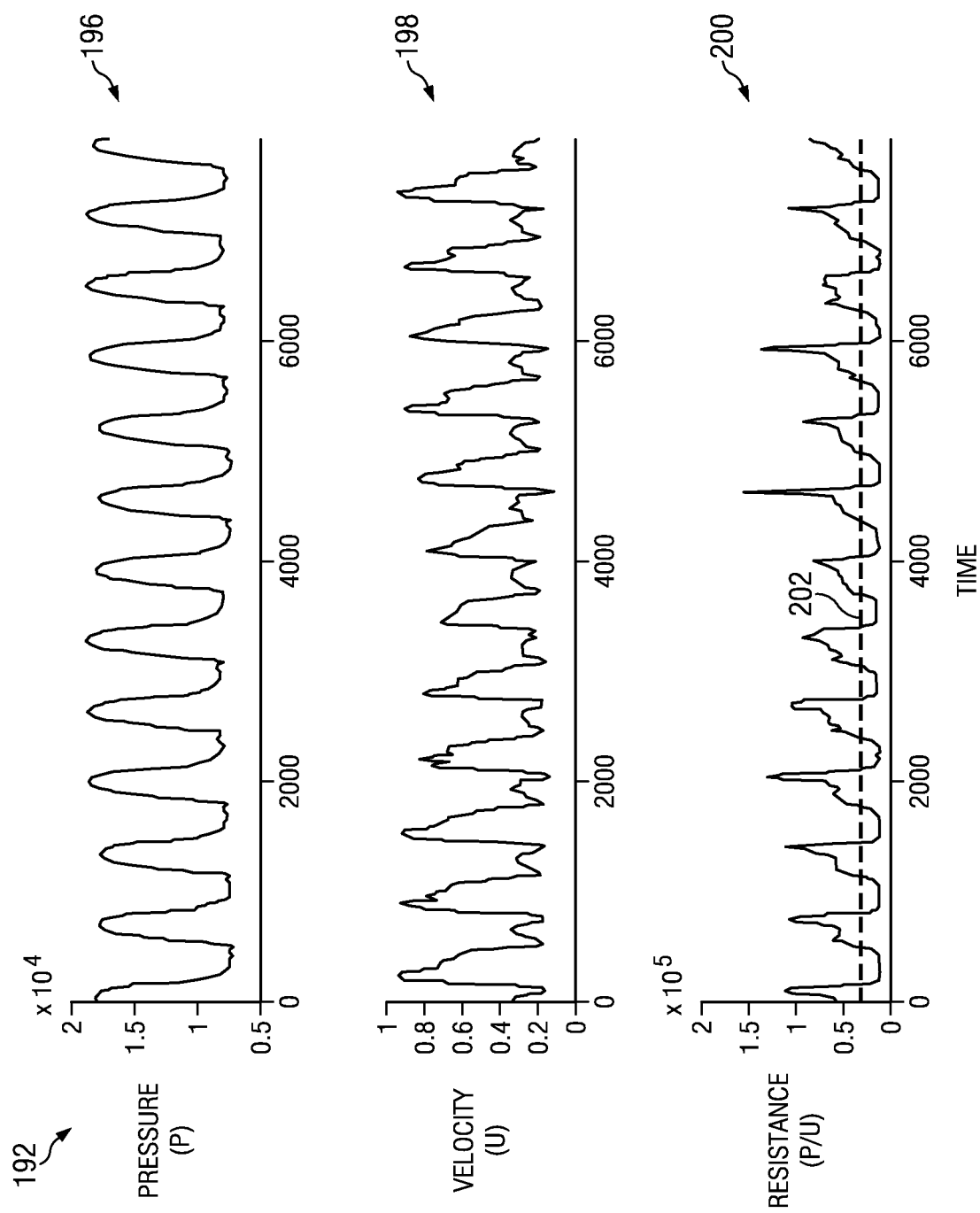
FIG. 6 is a magnified view of a portion of the graphical representation of FIG. 5 corresponding to a resting state of a patient.
Figure 7:
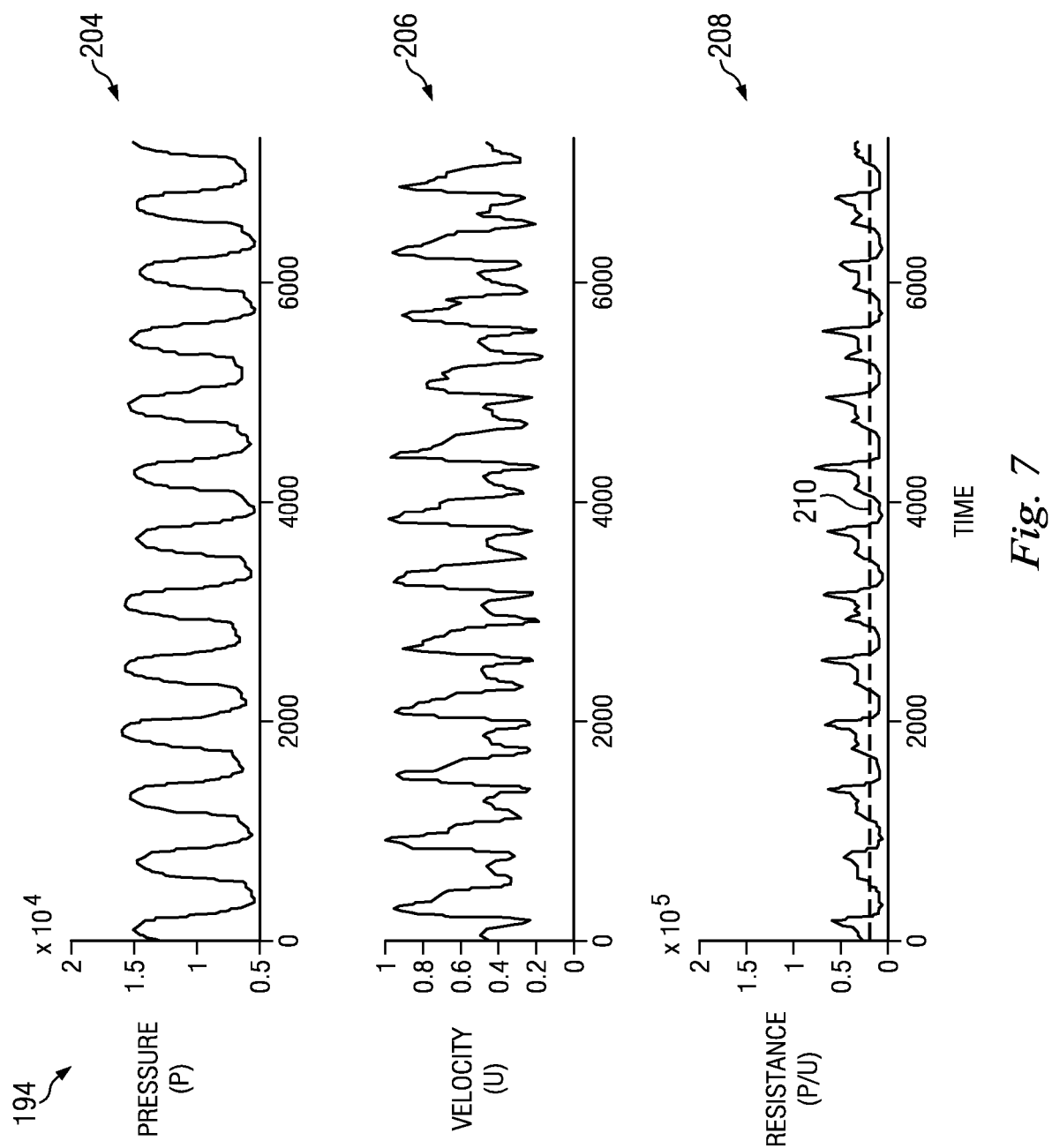
FIG. 7 is a magnified view of a portion of the graphical representation of FIG. 5 corresponding to a hyperemic state of a patient.
Figure 8:
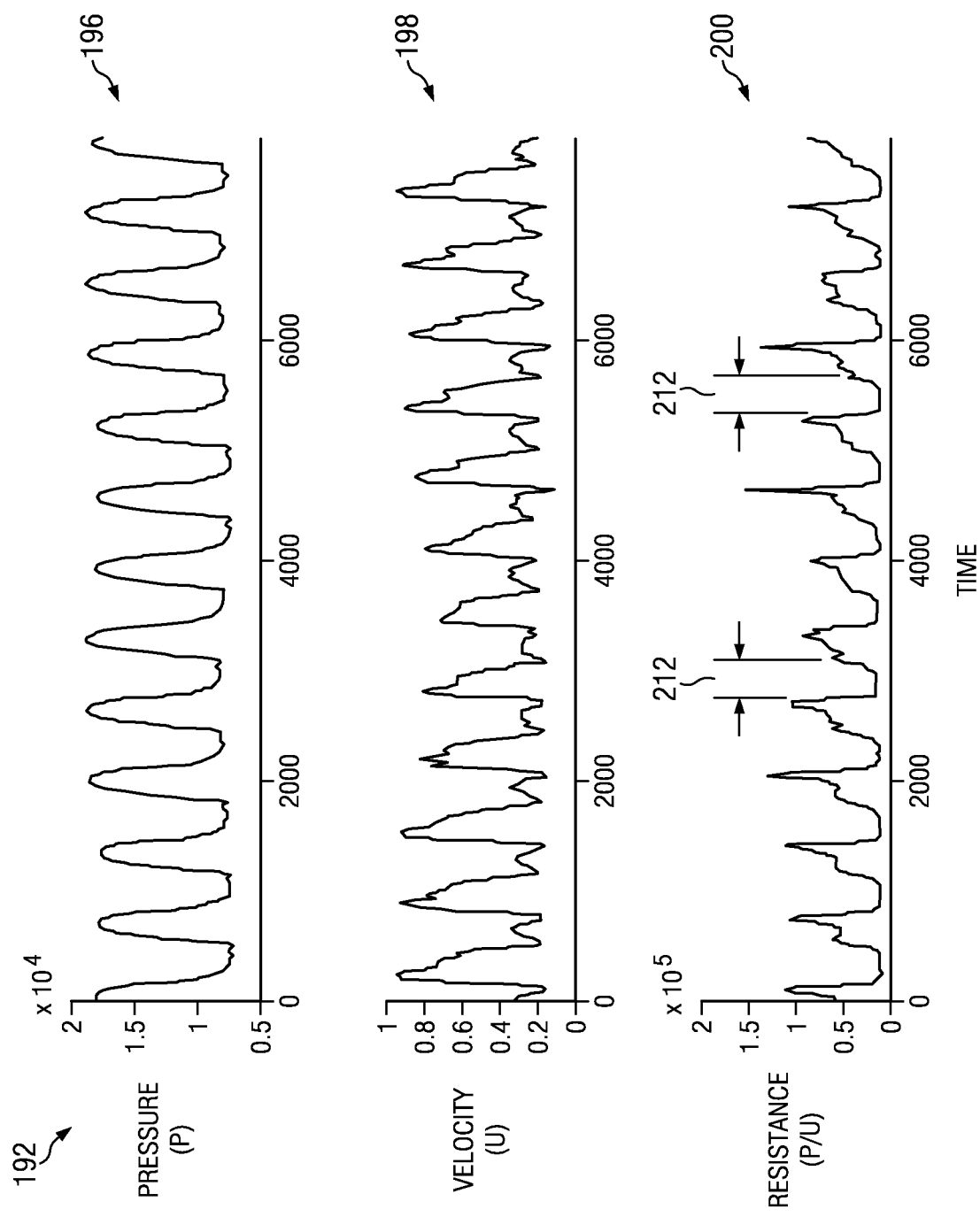
FIG. 8 is the portion of the graphical representation of FIG. 6 annotated to identify a diagnostic window according to an embodiment of the present disclosure.

Referring now to FIGS. 5-8, shown therein are graphical representations of diagnostic information illustrating aspects of an embodiment of the present disclosure. In that regard, FIG. 5 is a graphical representation of measured pressure, velocity, and resistance within a vessel; FIG. 6 is a magnified view of a portion of the graphical representation of FIG. 5 corresponding to a resting state of a patient; FIG. 7 is a magnified view of a portion of the graphical representation of FIG. 5 corresponding to a hyperemic state of a patient; and FIG. 8 is the portion of the graphical representation of FIG. 6 annotated to identify a diagnostic window according to an embodiment of the present disclosure.

Referring more particularly to FIG. 5, shown therein is a graphical representation 180 of diagnostic information pertaining to a vessel. More specifically, the graphical representation 180 includes a graph 182 plotting pressure within the vessel over time, a graph 184 plotting velocity of the fluid within the vessel over time, and a graph 186 plotting resistance within the vessel over time. In that regard, the resistance (or impedance) shown in graph 186 is calculated based on the pressure and velocity data of graphs 182 and 184. In particular, the resistance values shown in graph 186 are determined by dividing the pressure measurement of graph 182 by the velocity measurement 184 for the corresponding point in time. The graphical representation 180 includes a time period 188 that corresponds to a resting state of the patient's heart and a time period 190 that corresponds to a stressed state of the patient's heart. In that regard, the stressed state of the patient's heart is caused by the administration of a hyperemic agent in some instances.

To better illustrate the differences in the pressure, velocity, and resistance data between the resting and stressed states of the patient, close-up views of the data within windows 192 and 194 are provided in FIGS. 6 and 7. Referring more specifically to FIG. 6, window 192 of the graphical representation 180 includes graph portions 196, 198, and 200 that correspond to graphs 182, 184, and 186, respectively. As shown, in the resting state of FIG. 6, the resistance within the vessel has an average value of approximately 0.35 on the scale of graph 200, as indicated by line 202. Referring now to FIG. 7, window 194 of the graphical representation 180 includes graph portions 204, 206, and 208 that correspond to graphs 182, 184, and 186, respectively. As shown, in the stressed state of FIG. 7, the resistance within the vessel is significantly less than the resting state with a value of approximately 0.20 on the scale of graph 208, as indicated by line 210. As current FFR techniques rely on the average pressures across an entire heartbeat cycle, it is necessary to stress the patient's heart to achieve this reduced and relatively constant resistance across the entire heartbeat so that the data obtained is suitable for use with FFR techniques.

Referring to FIG. 8, similar to FIG. 6 window 192 of the graphical representation 180 of FIG. 5 is shown and includes graph portions 196, 198, and 200 that correspond to graphs 182, 184, and 186, respectively. However, in FIG. 8 a section 212 of the heartbeat cycle of the patient has been identified. As shown, section 212 corresponds to the portion of the heartbeat cycle of the patient where the resistance is reduced without the use of a hyperemic agent or other stressing technique. That is, section 212 is a portion of the heartbeat cycle of a resting patient that has a naturally reduced and relatively constant resistance. In other instances, section 212 of the heartbeat cycle encompasses the portion the heartbeat cycle that is less than a fixed percentage of the maximum resistance of the heartbeat cycle. In that regard, the fixed percentage of the maximum resistance of the heartbeat cycle is less than 50%, less than 30%, less than 25%, less than 20%, less than 15%, less than 10%, and less than 5% in some embodiments. In yet other instances, section 212 of the heartbeat cycle encompasses the portion the heartbeat cycle that is less than a fixed percentage of the average resistance of the heartbeat cycle. In that regard, the fixed percentage of the average resistance of the heartbeat cycle is less than 75%, less than 50%, less than 25%, less than 20%, less than 15%, less than 10%, and less than 5% in some embodiments.

Accordingly, in some embodiments of the present disclosure, the portion of the heartbeat cycle coinciding with section 212 is utilized as a diagnostic window for evaluating a stenosis of the vessel of a patient without the use of a hyperemic agent or other stressing of the patient's heart. In particular, the pressure ratio (distal pressure divided by proximal pressure) across the stenosis is calculated for the time period corresponding to section 212 for one or more heartbeats. The calculated pressure ratio is an average over the diagnostic window defined by section 212 in some instances. By comparing the calculated pressure ratio to a threshold or predetermined value, a physician or other treating medical personnel can determine what, if any, treatment should be administered. In that regard, in some instances, a calculated pressure ratio above a threshold value (e.g., 0.80 on a scale of 0.00 to 1.00) is indicative of a first treatment mode (e.g., no treatment, drug therapy, etc.), while a calculated pressure ratio below the threshold value is indicative of a second, more invasive treatment mode (e.g., angioplasty, stent, etc.). In some instances, the threshold value is a fixed, preset value. In other instances, the threshold value is selected for a particular patient and/or a particular stenosis of a patient. In that regard, the threshold value for a particular patient may be based on one or more of empirical data, patient characteristics, patient history, physician preference, available treatment options, and/or other parameters.

In some instances, section 212 is identified by monitoring pressure and fluid flow velocity within the vessel using one or more instruments and calculating the resistance within the vessel based on the measured pressure and velocity. For example, referring again to the embodiment of FIG. 3, in some instances the instrument 130 includes one or more sensing elements configured to monitor at least pressure and flow velocity, while instrument 132 includes one or more sensing elements configured to monitor at least pressure. Accordingly, with the one or more sensing elements of instrument 130 positioned distal of the stenosis and the one or more sensing elements of instrument 132 positioned proximal of the stenosis, the pressure and flow velocity measurements obtained by instrument 130 are utilized to identify section 212. Based on the identification of section 212, then the corresponding distal pressure measurements (as obtained by the one or more sensing elements of instrument 130) are compared to the proximal pressure measurements (as obtained by the one or more sensing elements of instrument 132) to calculate the pressure ratio across the stenosis during the diagnostic window defined by section 212. Additional examples of evaluating a vessel based on pressure and flow velocity measurements are described in UK Patent Application No. 1003964.2 filed Mar. 10, 2010 and titled "METHOD AND APPARATUS FOR THE MEASUREMENT OF A FLUID FLOW RESTRICTION IN A VESSEL", which is hereby incorporated by reference in its entirety.

In other instances, section 212 is identified without monitoring fluid velocity. In that regard, several techniques for identifying suitable diagnostic windows for use in evaluating a stenosis of a vessel based on pressure ratio across the stenosis without the use of hyperemic agents are described below. In some instances, the diagnostic window is identified solely based on characteristics of the pressure measurements obtained by instruments positioned within the vessel. Accordingly, in such instances, the instruments utilized need only have elements configured to monitor a pressure within the vessel, which results in reduced cost and simplification of the system. Exemplary techniques for evaluating a vessel based on pressure measurements are described in UK Patent Application No. 1100137.7 filed Jan. 6, 2011 and titled "APPARATUS AND METHOD OF ASSESSING A NARROWING IN A FLUID FILLED TUBE", which is hereby incorporated by reference in its entirety.

In general, the diagnostic window for evaluating differential pressure across a stenosis without the use of a hyperemic agent in accordance with the present disclosure may be identified based on characteristics and/or components of one or more of proximal pressure measurements, distal pressure measurements, proximal velocity measurements, distal velocity measurements, ECG waveforms, and/or other identifiable and/or measurable aspects of vessel performance. In that regard, various signal processing and/or computational techniques can be applied to the characteristics and/or components of one or more of proximal pressure measurements, distal pressure measurements, proximal velocity measurements, distal velocity measurements, ECG waveforms, and/or other identifiable and/or measurable aspects of vessel performance to identify a suitable diagnostic window.

In some embodiments, the determination of the diagnostic window and/or the calculation of the pressure differential are performed in approximately real time or live to identify the section 212 and calculate the pressure ratio. In that regard, calculating the pressure ratio in "real time" or "live" within the context of the present disclosure is understood to encompass calculations that occur within 10 seconds of data acquisition. It is recognized, however, that often "real time" or "live" calculations are performed within 1 second of data acquisition. In some instances, the "real time" or "live" calculations are performed concurrent with data acquisition. In some instances the calculations are performed by a processor in the delays between data acquisitions. For example, if data is acquired from the pressure sensing devices for 1 ms every 5 ms, then in the 4 ms between data acquisitions the processor can perform the calculations. It is understood that these timings are for example only and that data acquisition rates, processing times, and/or other parameters surrounding the calculations will vary. In other embodiments, the pressure ratio calculation is performed 10 or more seconds after data acquisition. For example, in some embodiments, the data utilized to identify the diagnostic window and/or calculate the pressure ratio are stored for later analysis.

Figure 9:
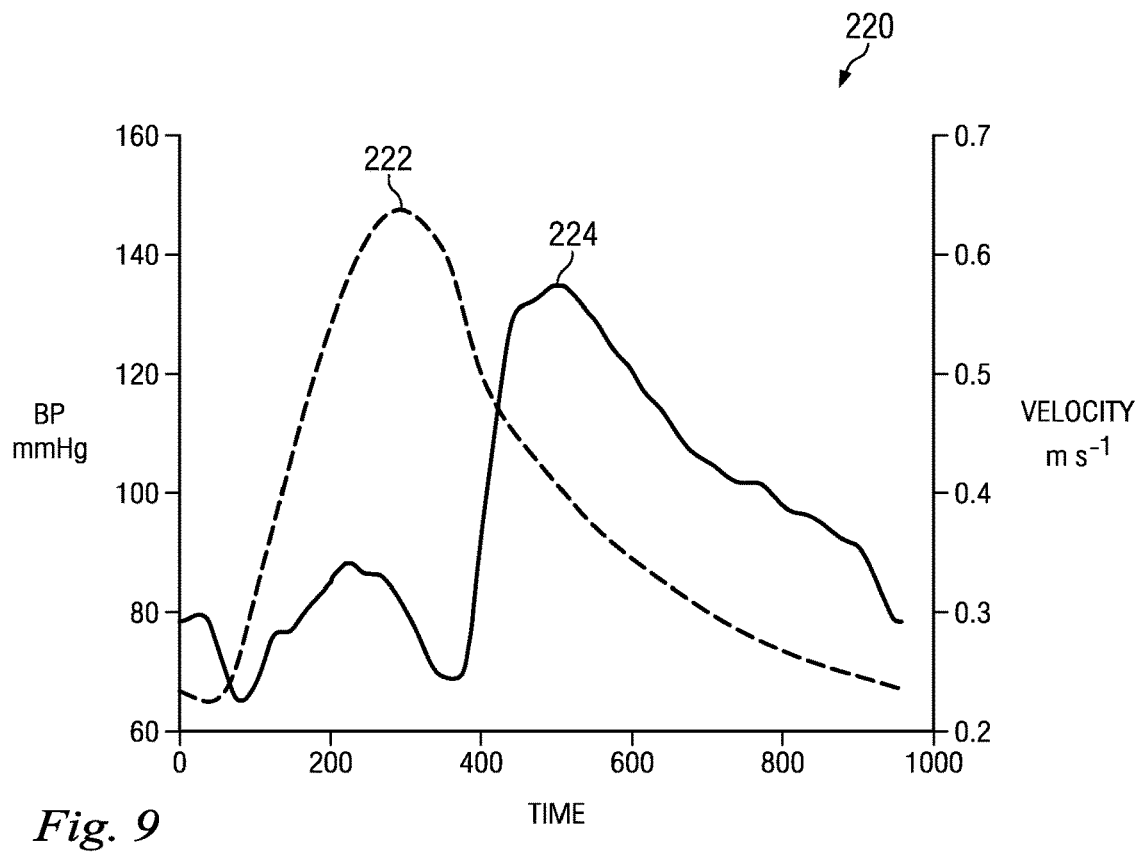
FIG. 9 is a graphical representation of measured pressure and velocity within a vessel according to an embodiment of the present disclosure.
Figure 10:
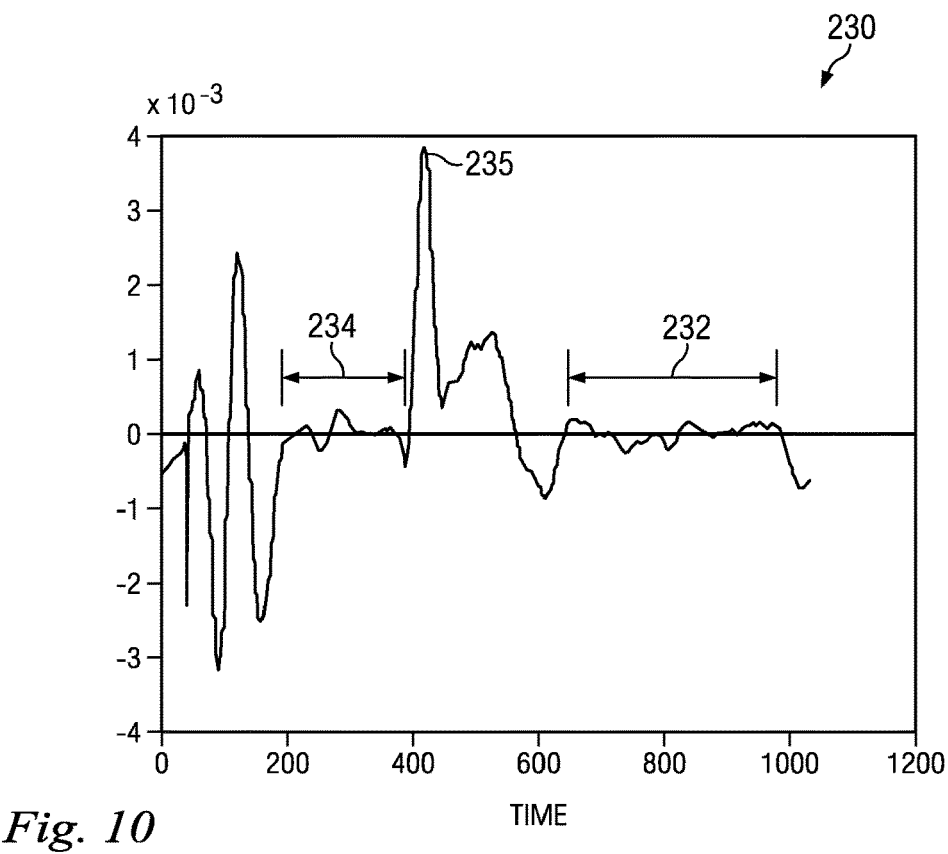
FIG. 10 is a graphical representation of a derivative of the measured velocity of FIG. 9 according to an embodiment of the present disclosure.
Figure 11:
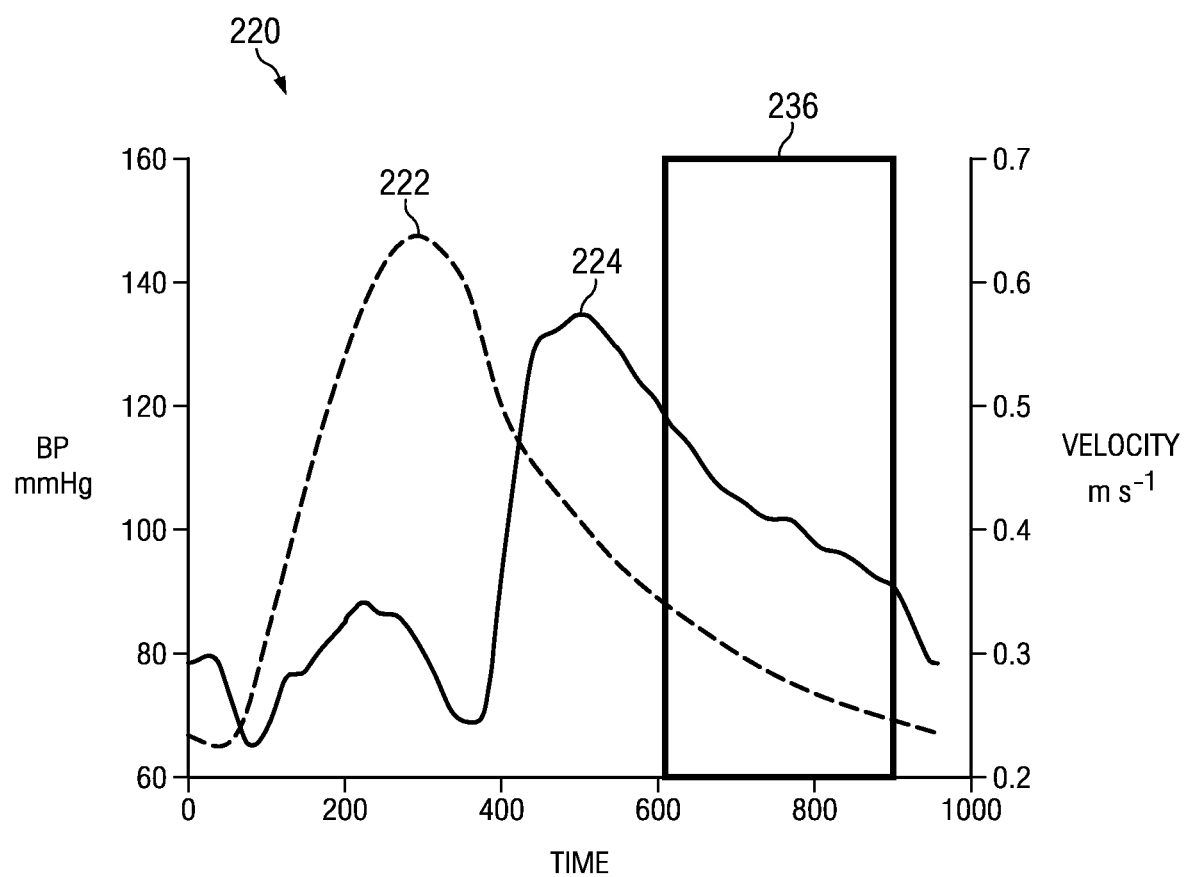
FIG. 11 is the graphical representation of FIG. 9 annotated to identify a diagnostic window according to an embodiment of the present disclosure.

Referring now to FIGS. 9-11, shown therein are graphical representations of diagnostic information illustrating aspects of another embodiment of the present disclosure. In that regard, FIG. 9 is a graphical representation of measured pressure and velocity within a vessel; FIG. 10 is a graphical representation of a differential of the measured velocity of FIG. 9; and FIG. 11 is the graphical representation of measured pressure and velocity within the vessel annotated to identify a diagnostic window according to an embodiment of the present disclosure.

Referring more specifically to FIG. 9, graphical representation 220 includes a plot 222 representative of pressure (measured in mmHg) within a vessel over the time period of one cardiac cycle and a plot 224 representative of velocity (measured in m/s) of a fluid within the vessel over the same cardiac cycle. FIG. 10, in turn, is a graphical representation 230 of a differential of the velocity plot 224 of graphical representation 220 of FIG. 9. In that regard, in some instances, the velocity differential or change in velocity (dU) is calculated as $$dU_{xy} = \frac{U_x - U_y}{t},$$

where $U_x$ is the velocity at time x, $U_y$ is the velocity at time y, and t is the elapsed time between $U_x$ and $U_y$. In some instances, the variable t is equal to the sample rate of the velocity measurements of the system such that the differential is calculated for all data points. In other instances, the variable t is longer than the sample rate of the velocity measurements of the system such that only a subset of the obtained data points are utilized.

As shown in FIG. 10, for a time period 232 extending from about 625 ms to about 1000 ms the differential of the velocity plot 224 is relatively stabilized around zero. In other words, the velocity of the fluid within the vessel and/or the vascular resistance is relatively constant during time period 232. In some instances, the velocity is considered stabilized when it varies between −0.01 and +0.01, and in some specific instance is considered stabilized when it varies between about −0.005 and about +0.005. However, in other instances, the velocity is considered stabilized with values outside of these ranges. Similarly, for a time period 234 extending from about 200 ms to about 350 ms the differential of the velocity plot 224 is relatively stabilized around zero representing that the velocity of the fluid within the vessel is substantially constant during time period 234 as well. However, time period 234 can be highly variable, as valvular disease, dyssynchrony within a ventricle, regional myocardial contractile differences, microvascular disease can all lead to large variations of timing of the time period 234. As discussed below, all or portions of the time periods 232 and/or 234 are utilized as a diagnostic window for evaluating pressure ratio across a stenosis in some embodiments of the present disclosure. In that regard, the diagnostic window is selected by identifying a portion of the cardiac cycle corresponding to the time period in which the change in velocity (i.e., dU) fluctuates around zero. FIG. 11 shows the graphical representation 220 of FIG. 9 annotated to identify a diagnostic window 236 corresponding to the time period 232 of FIG. 10. In other instances, the diagnostic window is selected by identifying a portion of the cardiac cycle corresponding to a period in which the change in velocity (i.e., dU) is relatively small compared to the maximum change in velocity (i.e., $dU_{max}$) during a cardiac cycle. In the illustrated embodiment of FIG. 10, the maximum change in velocity (i.e., $dU_{max}$) occurs at point 235. In some instances, the diagnostic window is selected by identifying the portion(s) of the cardiac cycle where the change in velocity (i.e., dU) is less than 25%, less than 20%, less than 15%, less than 10%, and/or less than 5% of the maximum change in velocity (i.e., $dU_{max}$) for the cardiac cycle.

There are a variety of signal processing techniques that can be utilized to identify time period 232, time period 234, and/or other time periods where the change in velocity is relatively constant and approximately zero, such as variation or standard deviation from the mean, minimum threshold offset, or otherwise. Further, while time periods 232 and 234 have been identified using a differential of the velocity measurement, in other instances first, second, and/or third derivatives of the velocity measurement are utilized. For example, identifying time periods during the cardiac cycle where the first derivative of velocity is relatively constant and approximately zero allows the localization of time periods where velocity is relatively constant. Further, identifying time periods during the cardiac cycle where the second derivative of velocity is relatively constant and approximately zero allows the localization of a time period where acceleration is relatively constant and near zero, but not necessarily zero.

Time periods 232, 234, and/or other time periods where the change in velocity is relatively constant and approximately zero (i.e., the speed of the fluid flow is stabilized) are suitable diagnostic windows for evaluating a pressure differential across a stenosis of a vessel without the use of a hyperemic agent in accordance with the present disclosure. In that regard, in a fluid flow system, the separated forward and backward generated pressures are defined by:

$$dP_+ = \frac{1}{2}(dP + \rho c dU) \text{ and } dP_- = \frac{1}{2}(dP - \rho c dU),$$

where dP is the differential of pressure, ρ is the density of the fluid within the vessel, c is the wave speed, and dU is the differential of flow velocity. However, where the flow velocity of the fluid is substantially constant, dU is approximately zero and the separated forward and backward generated pressures are defined by:

$$dP_+ = \frac{1}{2}(dP + \rho c(0)) = \frac{1}{2}dP \text{ and } dP_- = \frac{1}{2}(dP - \rho c(0)) = \frac{1}{2}dP.$$

In other words, during the time periods where dU is approximately zero, the forward and backward generated pressures are defined solely by changes in pressure.

Accordingly, during such time periods the severity of a stenosis within the vessel can be evaluated based on pressure measurements taken proximal and distal of the stenosis. In that regard, by comparing the forward and/or backward generated pressure distal of a stenosis to the forward and/or backward generated pressure proximal of the stenosis, an evaluation of the severity of the stenosis can be made. For example, the forward-generated pressure differential can be calculated as $$\frac{dP_{+distal}}{dP_{+proximal}},$$

while the backward-generated pressure differential can be calculated as $$\frac{dP_{-distal}}{dP_{-proximal}}.$$

In the context of the coronary arteries, a forward-generated pressure differential is utilized to evaluate a stenosis in some instances. In that regard, the forward-generated pressure differential is calculated based on proximally originating (i.e., originating from the aorta) separated forward pressure waves and/or reflections of the proximally originating separated forward pressure waves from vascular structures distal of the aorta in some instances. In other instances, a backward-generated pressure differential is utilized in the context of the coronary arteries to evaluate a stenosis. In that regard, the backward-generated pressure differential is calculated based on distally originating (i.e., originating from the microvasculature) separated backward pressure waves and/or reflections of the distally originating separated backward pressure waves from vascular structures proximal of the microvasculature.

In yet other instances, a pressure wave is introduced into the vessel by an instrument or medical device. In that regard, the instrument or medical device is utilized to generate a proximally originating forward pressure wave, a distally originating backward pressure wave, and/or combinations thereof for use in evaluating the severity of the stenosis. For example, in some embodiments an instrument having a movable membrane is positioned within the vessel. The movable membrane of the instrument is then activated to cause movement of the membrane and generation of a corresponding pressure wave within the fluid of the vessel. Based on the configuration of the instrument, position of the membrane within the vessel, and/or the orientation of the membrane within the vessel the generated pressure wave(s) will be directed distally, proximally, and/or both. Pressure measurements based on the generated pressure wave(s) can then be analyzed to determine the severity of the stenosis.

Figure 12:
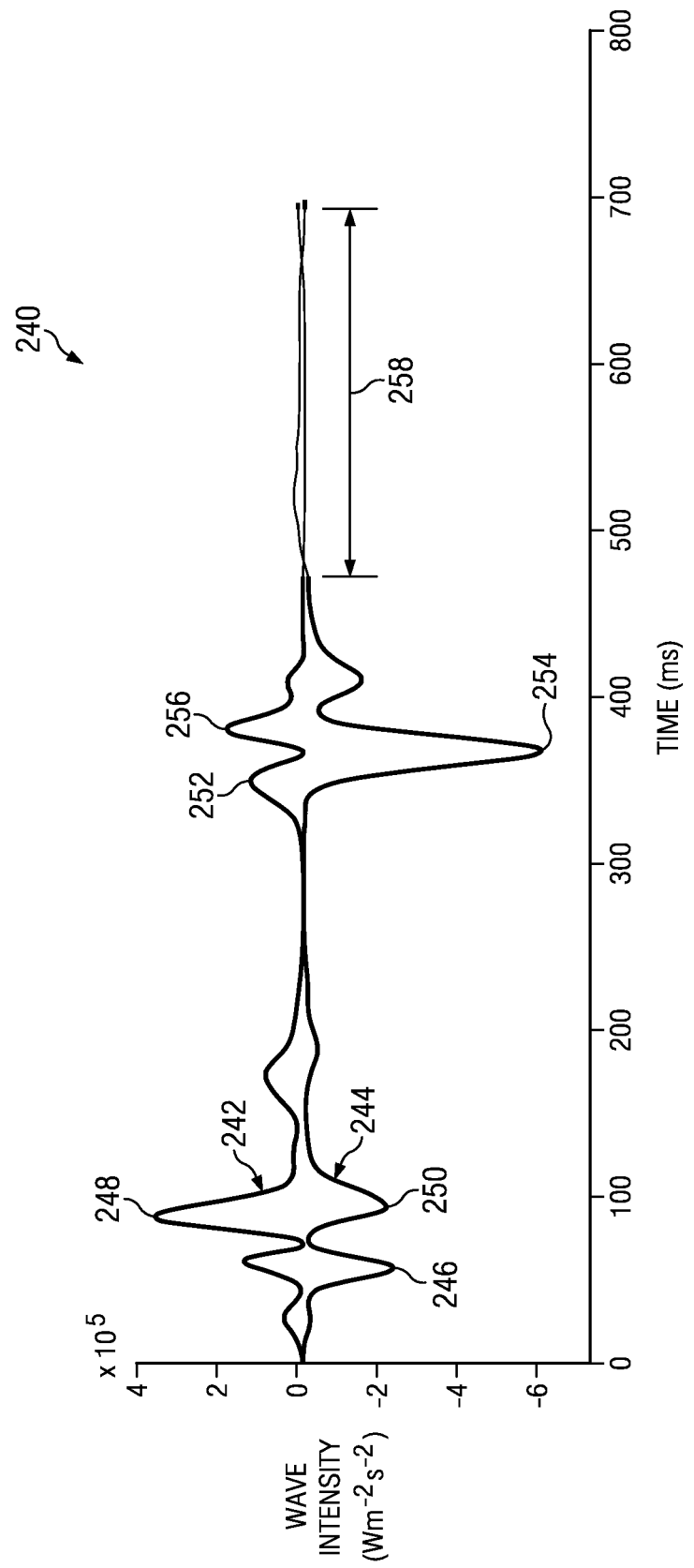
FIG. 12 is a graphical representation of wave intensity within a vessel according to an embodiment of the present disclosure.
Figure 13:
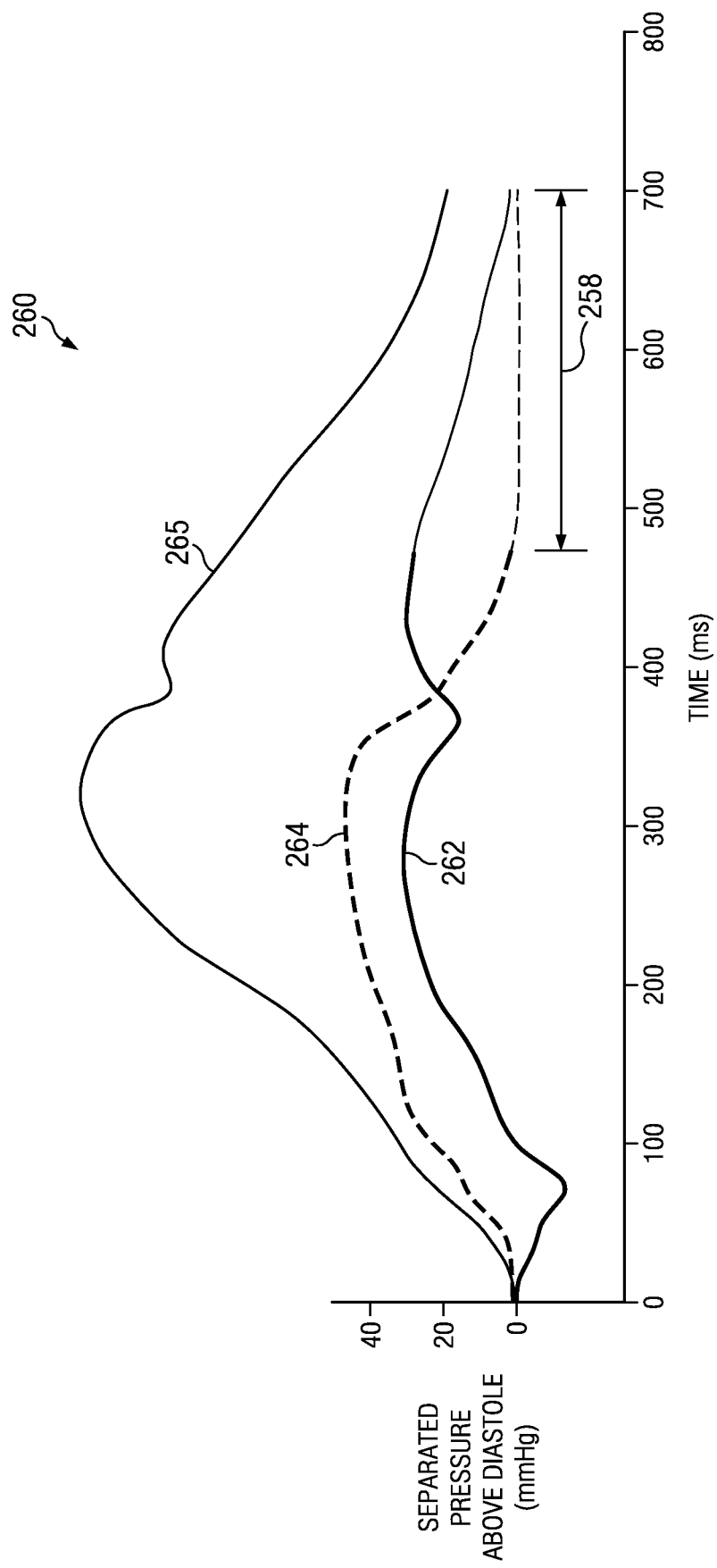
FIG. 13 is a graphical representation of proximal and distal originating pressure waves within a vessel corresponding to the wave intensity of FIG. 12 according to an embodiment of the present disclosure.
Figure 14:
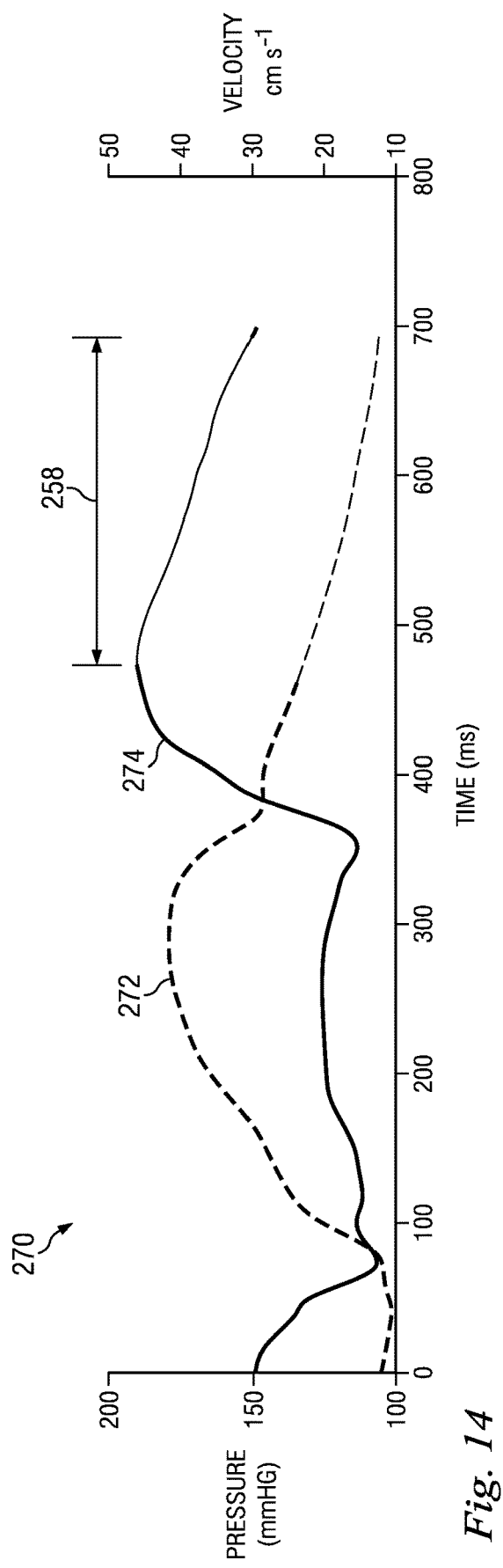
FIG. 14 is a graphical representation of pressure and velocity within a vessel corresponding to the wave intensity of FIG. 12 and the proximal and distal originating pressure waves of FIG. 13 according to an embodiment of the present disclosure.
Figure 15:
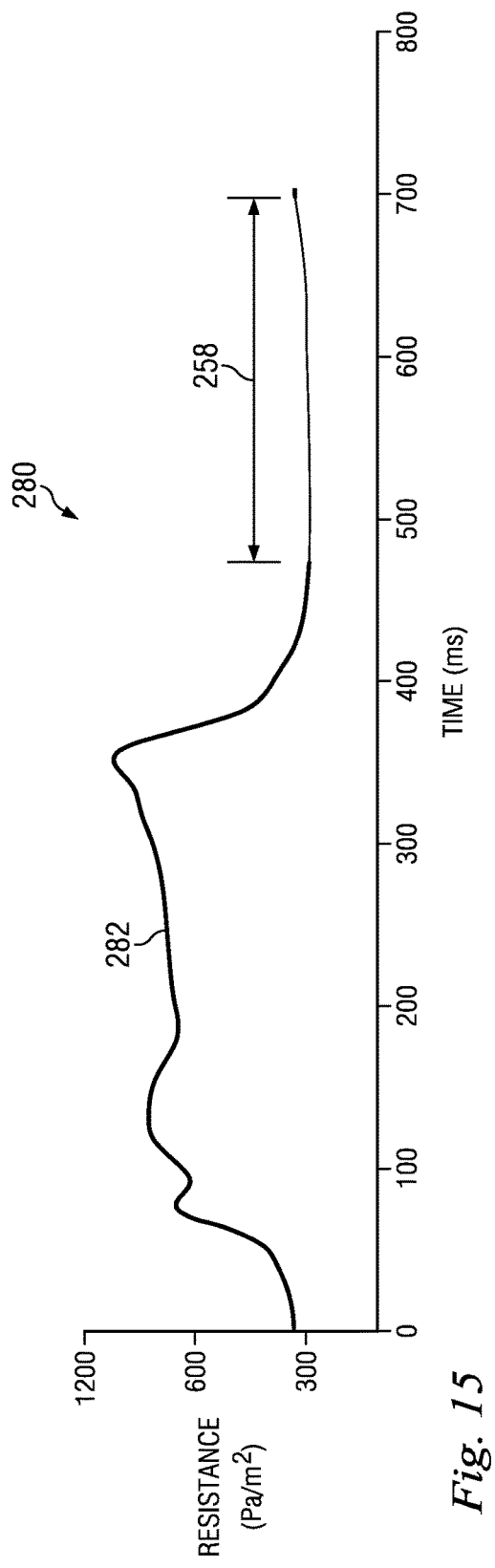
FIG. 15 is a graphical representation of a resistance within a vessel corresponding to the wave intensity of FIG. 12, the proximal and distal originating pressure waves of FIG. 13, and the pressure and velocity of FIG. 14 according to an embodiment of the present disclosure.

Referring now to FIGS. 12-15, shown therein are graphical representations of diagnostic information illustrating aspects of another embodiment of the present disclosure. In that regard, FIG. 12 is a graphical representation of wave intensity within a vessel; FIG. 13 is a graphical representation of proximal and distal originating pressure waves within the vessel corresponding to the wave intensity of FIG. 12; FIG. 14 is a graphical representation of pressure and velocity within the vessel corresponding to the wave intensity of FIG. 12 and the proximal and distal originating pressure waves of FIG. 13; and FIG. 15 is a graphical representation of a resistance within the vessel corresponding to the wave intensity of FIG. 12, the proximal and distal originating pressure waves of FIG. 13, and the pressure and velocity of FIG. 14.

Referring more specifically to FIG. 12, shown therein is a graphical representation 240 plotting the intensities associated with proximally and distally originating waves of a cardiac cycle over time. In that regard, plot 242 is representative of proximally originating waves, while plot 244 is representative of distally originating waves. As shown, six predominating waves are associated with the cardiac cycle of a patient. In order of occurrence during a cardiac cycle, wave 246 is a backward-traveling pushing wave, wave 248 is a dominant forward-traveling pushing wave, wave 250 is a backward-traveling pushing wave, wave 252 is a forward-traveling suction wave, wave 254 is a dominant backward-traveling suction wave, and wave 256 is a forward-traveling pushing wave. Notably, no waves are generated during a time period 258 late in the cardiac cycle. In some instances, the time period 258 is referred to as a wave-free period of the cardiac cycle. Additional details regarding pressure waves in the context of the coronary arteries can be found in "Evidence of a Dominant Backward-Propagating 'Suction' Wave Responsible for Diastolic Coronary Filling in Humans, Attenuated in Left Ventricular Hypertrophy" by Davies et al. (*Circulation*. 2006; 113:1768-1778), which is hereby incorporated by reference in its entirety.

Referring now to FIG. 13, shown therein is a graphical representation 260 of proximal and distal originating pressure waves within a vessel over a time period associated with a cardiac cycle. In that regard, the pressure waves of FIG. 13 correspond to the wave intensities of FIG. 12. As shown, the graphical representation 260 includes a plot 262 representative of a proximally-originating pressure, a plot 264 representative of a distally-originating pressure, and a plot 265 representative of the total pressure (proximally-originating pressure plus the distally-originating pressure).

Referring now to FIG. 14, shown therein is a graphical representation 270 that includes a plot 272 representative of pressure (measured in mmHg) within a vessel over time and a plot 274 representative of velocity (measured in cm/s) of a fluid within the vessel over time. In that regard, the pressure and velocity plots 272, 274 of FIG. 14 correspond to the wave intensities and pressure waves of FIGS. 12 and 13, respectively. As shown, for the wave-free time period 258 extending from about 475 ms to about 675 ms the slopes of the pressure plot 272 and the velocity plot 274 are relatively constant. At this time point, as shown in FIG. 15, the resistance within the vessel is relatively constant and reduced during the time period 258. In that regard, the graphical representation 280 of FIG. 15 includes a plot 282 of the resistance within the vessel over the time of a cardiac cycle. In that regard, the resistance values of graphical representation 280 are calculated using the pressure and velocity measurements of FIG. 14, where resistance is equal to pressure divided by velocity for a particular point in time along the cardiac cycle. Due to the reduced and relative constant resistance during time period 258, all or a portion of the time period 258 is suitable for use as a diagnostic window for evaluating pressure differential across a stenosis in some embodiments of the present disclosure. In that regard, in some embodiments the diagnostic window is the period of minimum resistance that corresponds to the wave-free period at the end of the backward-travelling suction wave, running to shortly before the end of the cardiac cycle.

Figure 23:
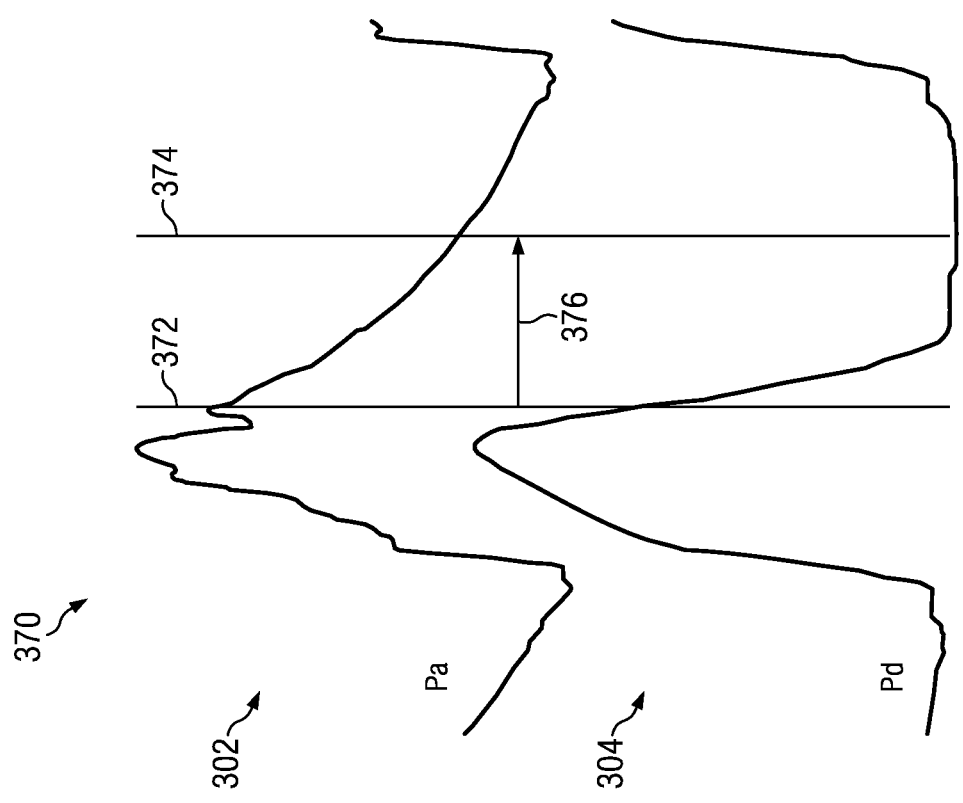
FIG. 23 is a graphical representation of an identification of an ending point of a diagnostic window based on a starting point of the diagnostic window according to an embodiment of the present disclosure.
Figure 26:
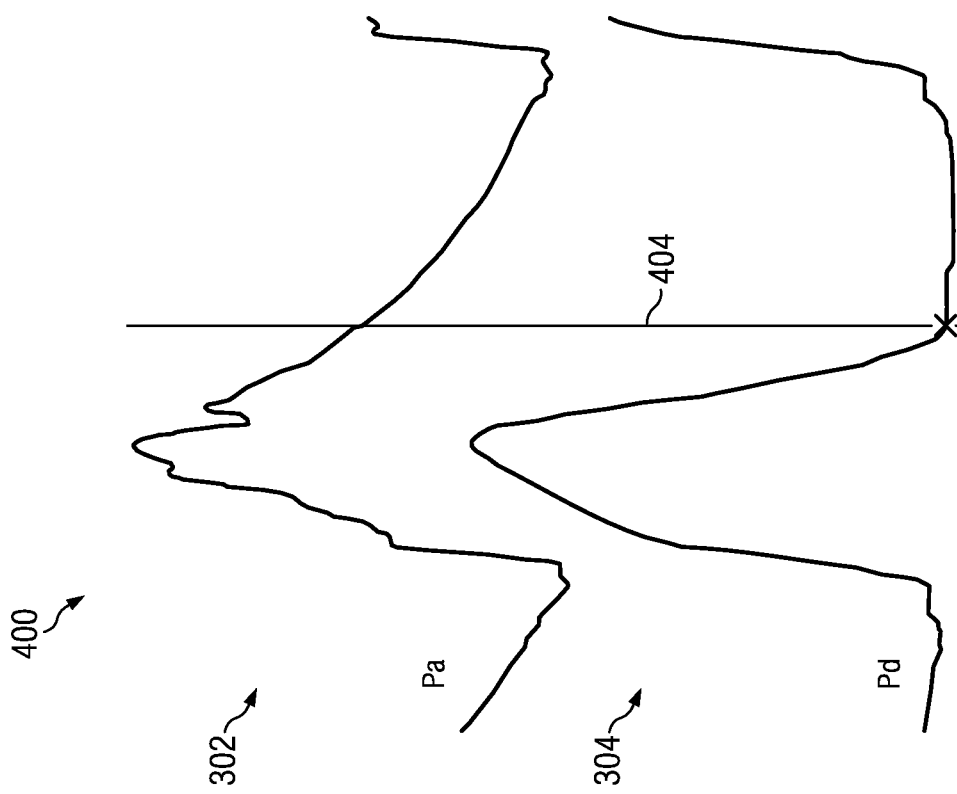
FIG. 26 is a graphical representation of an identification of an ending point of a diagnostic window based on a distal pressure measurement according to an embodiment of the present disclosure.

Referring now to FIGS. 16-26, shown therein are various graphical representations of techniques for determining start and/or end points for a diagnostic window in accordance with the present disclosure. In that regard, FIGS. 16-18 generally illustrate identification of a starting point of a diagnostic window based on a proximal pressure measurement; FIGS. 19-22 generally illustrate identification of a starting point of a diagnostic window based on a distal pressure measurement; FIG. 23 illustrates identification of an end of a diagnostic window based on a starting point of the diagnostic window; FIG. 24 illustrates identification of an ending point of a diagnostic window based on a proximal pressure measurement; and FIGS. 25 and 26 illustrate identification of an ending point of a diagnostic window based on a distal pressure measurement.

Figure 16:
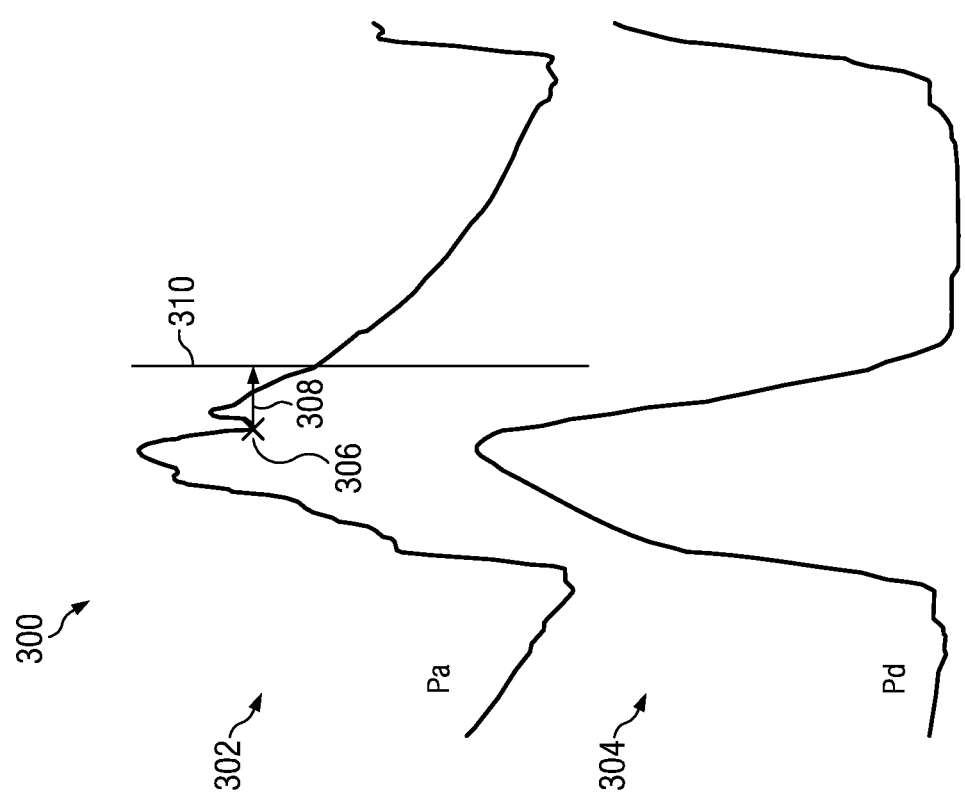
FIG. 16 is a graphical representation of an identification of a starting point of a diagnostic window based on a proximal pressure measurement according to an embodiment of the present disclosure.

As shown in FIG. 16, a graphical representation 300 includes a proximal pressure reading 302 and a distal pressure reading 304 each plotted over time relative to a cardiac cycle. In that regard, the proximal pressure reading 302 is representative of a pressure proximal of a stenosis of a vessel. The proximal pressure reading 302 is based upon a partial pressure (e.g., forward generated or backward generated) in some instances. Similarly, the distal pressure reading 304 is representative of a pressure distal of the stenosis. The distal pressure reading 304 is based upon a partial pressure (e.g., forward generated or backward generated) in some instances.

For simplicity and consistency, the proximal and distal pressure readings 302 and 304 provided in FIG. 16 will be utilized in describing the techniques associated with FIGS. 17-28 as well. However, with respect to all of the disclosed techniques the proximal and distal pressure readings 302 and 304 are exemplary and should not be considered limiting in any way. In that regard, it is understood that the pressure readings will vary from patient to patient and even between cardiac cycles of a single patient. Accordingly, it is understood that the techniques described herein for identifying a diagnostic window based on these pressure readings are suitable for use with a wide variety of pressure reading plots. Further, it is understood that the techniques described below are calculated or determined over a plurality of cardiac cycles in some instances. For example, in some embodiments the diagnostic window is identified by making calculations over a plurality of cardiac cycles and calculating an average or mean value, identifying overlapping areas common to the plurality of cardiac cycles, and/or otherwise identifying a suitable time period for a diagnostic window. Further still, it is understood that two or more of the techniques described below may be utilized together to identify a starting point, ending point, and/or other aspect of a diagnostic window.

Figure 17:
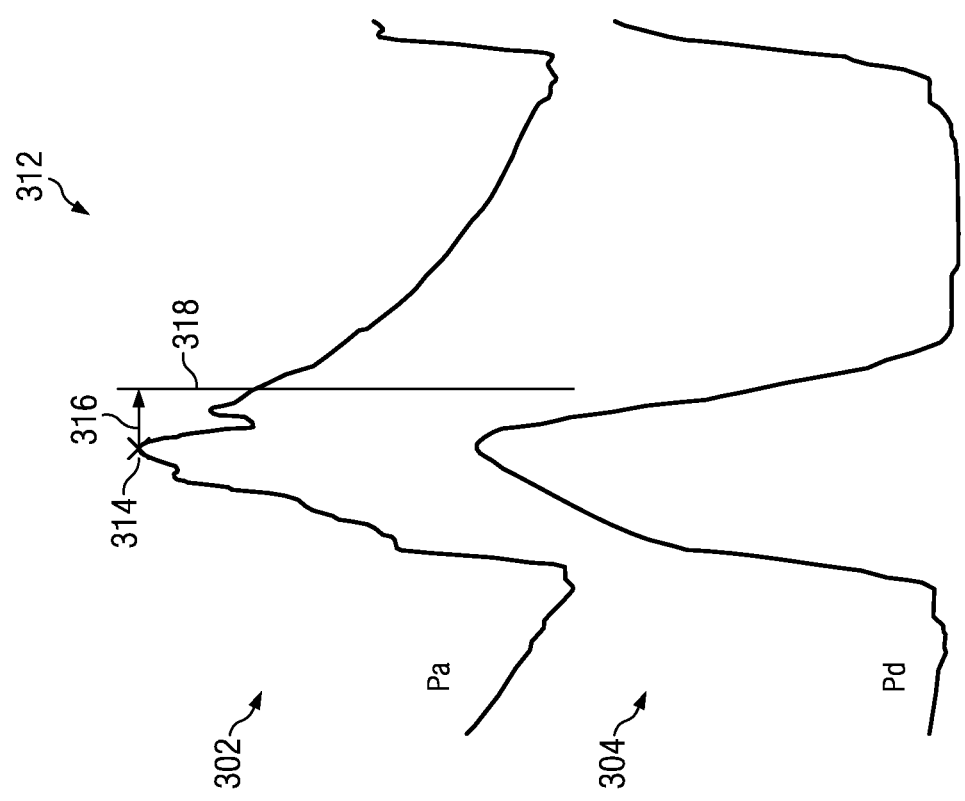
FIG. 17 is a graphical representation of an identification of a starting point of a diagnostic window based on a proximal pressure measurement according to another embodiment of the present disclosure.
Figure 18:
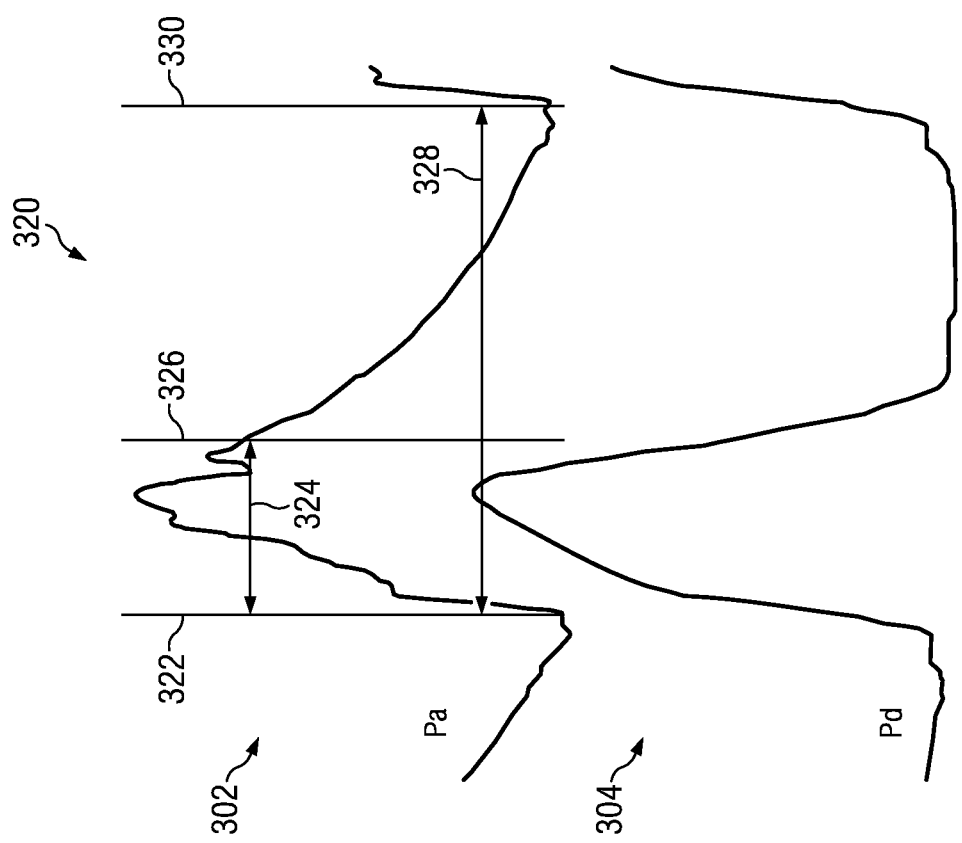
FIG. 18 is a graphical representation of an identification of a starting point of a diagnostic window based on a proximal pressure measurement according to another embodiment of the present disclosure.

Referring now to FIGS. 16-18, shown therein are several techniques for identifying a starting point of a diagnostic window based on a proximal pressure measurement. Referring more specifically to FIG. 16, the starting point of the diagnostic window is determined by identifying a dicrotic notch and adding a fixed amount of time in some instances. As shown in FIG. 16, a dicrotic notch 306 has been identified and a fixed time period 308 has been added to determine the starting point 310 of a diagnostic window. The fixed time period 308 is between about 1 ms and about 500 ms in some instances. In some particular instances, the time period 308 is between about 25 ms and about 150 ms. In other instances, the amount of time added to the start of diastole is selected based on a percentage of the cardiac cycle or a percentage of the length of diastole. For example, in some instances, the amount of time added is between about 0% and about 70% of the length of the cardiac cycle. In yet other instances, no time is added to the dicrotic notch, such that the dicrotic notch 306 is the starting point 310.

In another embodiment, a start of diastole is identified based on the proximal pressure measurements and a fixed time period is added to determine the starting point of a diagnostic window. The fixed time period is between about 1 ms and about 500 ms. In some particular embodiments, the fixed time period is between the beginning of diastole and the start of the diagnostic window is between about 25 ms and about 200 ms. In other instances, the amount of time added to the start of diastole is selected based on a percentage of the cardiac cycle or a percentage of the length of diastole. For example, in some instances, the time added to the start of diastole is between about 0% and about 70% of the cardiac cycle. In other instances, the time added to the start of diastole is between about 0% and about 100% of the total length of the diastole portion of the cardiac cycle. In some instances, the time added to the start of diastole is between about 2% and about 75% of the total length of the diastole portion of the cardiac cycle. In yet other instances, no time is added to the start of diastole, such that the start of diastole is also the starting point of the diagnostic window.

Referring now to FIG. 17, the starting point of the diagnostic window is determined by identifying a peak proximal pressure and adding a fixed amount of time in some instances. As shown in the graphical representation 312 of FIG. 17, a peak pressure 314 has been identified and a fixed time period 316 has been added to determine the starting point 318 of a diagnostic window. The fixed time period 316 is between about 1 ms and about 550 ms in some instances. In some instances, the fixed time period 316 is between about 25 ms and about 175 ms. In other instances, the amount of time added to the peak proximal pressure is selected based on a percentage of the cardiac cycle or a percentage of the length of diastole. For example, in some instances, the amount of time added is between about 0% and about 70% of the length of the cardiac cycle. In yet other instances, no time is added to the peak proximal pressure, such that the peak pressure 314 is the starting point 318.

Referring now to FIG. 18, the starting point of the diagnostic window is determined by identifying the start of a cardiac cycle and adding a fixed amount of time in some instances. As shown in the graphical representation 320 of FIG. 18, a start 322 of the cardiac cycle has been identified and a fixed time period 324 has been added to determine the starting point 326 of a diagnostic window. The fixed time period 324 is between about 150 ms and about 900 ms in some instances. In some instances, the fixed time period 324 is between about 300 ms and about 600 ms. In some particular embodiments, the fixed time period 324 is calculated as a percentage of the length 328 of a cardiac cycle of the patient. As shown in FIG. 18, an end 330 of the cardiac cycle has been identified such that the length 328 of the cardiac cycle extends between the start 322 and the end 330. The percentage of the length 328 of the cardiac cycle utilized for calculating the starting point 356 is between about 25% and about 95% in some instances. In some instances, the percentage of the length 328 of the cardiac cycle is between about 40% and about 75%. In yet other instances, no time is added to the start of the cardiac cycle, such that the start of the cardiac cycle 322 is the starting point 326.

Figure 19:
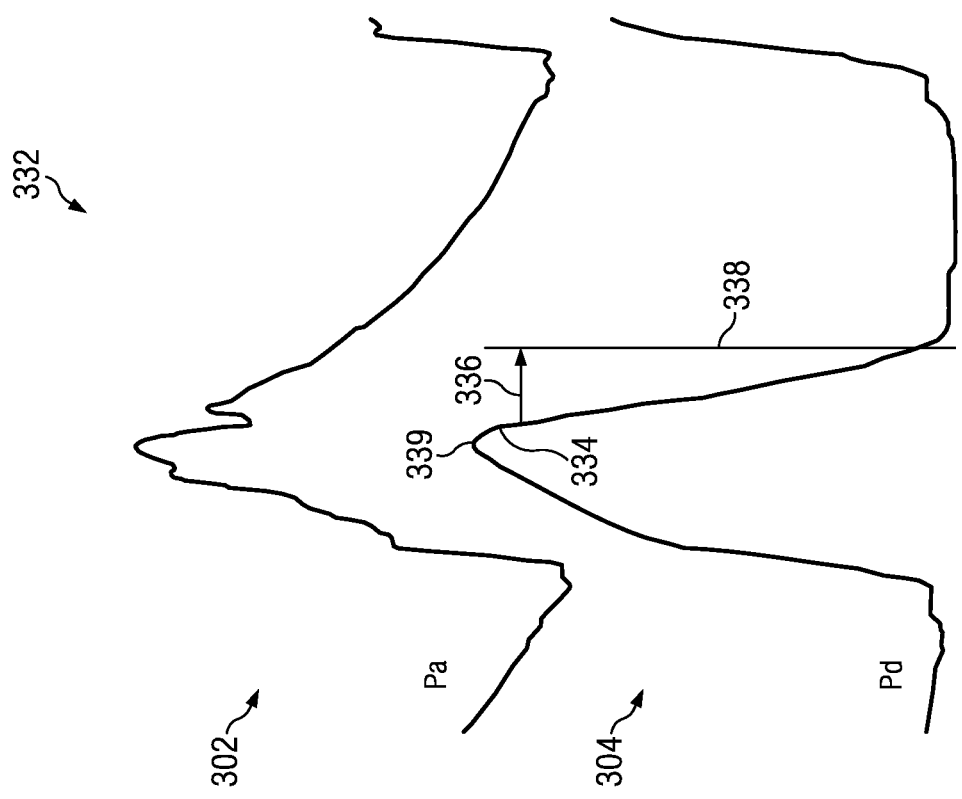
FIG. 19 is a graphical representation of an identification of a starting point of a diagnostic window based on a distal pressure measurement according to an embodiment of the present disclosure.

Referring now to FIGS. 19-22, shown therein are several techniques for identifying a starting point of a diagnostic window based on a distal pressure measurement. Referring more specifically to FIG. 19, the starting point of the diagnostic window is determined by identifying a dicrotic notch and adding a fixed amount of time in some instances. As shown in the graphical representation 332 of FIG. 19, a dicrotic notch 334 has been identified and a fixed time period 336 has been added to determine the starting point 338 of a diagnostic window. The fixed time period 336 is between about 1 ms and about 500 ms in some instances. In some instances, the fixed time period 336 is between about 25 ms and about 150 ms. In other instances, a peak pressure 339 is identified based on the distal pressure measurements and a fixed time period is added to determine the starting point of a diagnostic window. The fixed time period relative to the peak pressure is between about 1 ms and about 550 ms in some instances. In some instances, the fixed time period is between about 25 ms and about 175 ms. In yet other instances, no time is added to the dicrotic notch, such that the dicrotic notch 334 is the starting point 338.

In another embodiment, a start of diastole is identified based on the distal pressure measurements and a fixed time period is added to determine the starting point of a diagnostic window. The fixed time period is between about 1 ms and about 500 ms. In some particular embodiments, the fixed time period between the beginning of diastole and the start of the diagnostic window is between about 25 ms and about 200 ms. In other instances, the amount of time added to the start of diastole is selected based on a percentage of the cardiac cycle or a percentage of the length of diastole. For example, in some instances, the time added to the start of diastole is between about 0% and about 70% of the cardiac cycle. In other instances, the time added to the start of diastole is between about 0% and about 100% of the total length of the diastole portion of the cardiac cycle. In some instances, the time added to the start of diastole is between about 2% and about 75% of the total length of the diastole portion of the cardiac cycle. In yet other instances, no time is added to the start of diastole, such that the start of diastole is the starting point of the diagnostic window.

Figure 20:
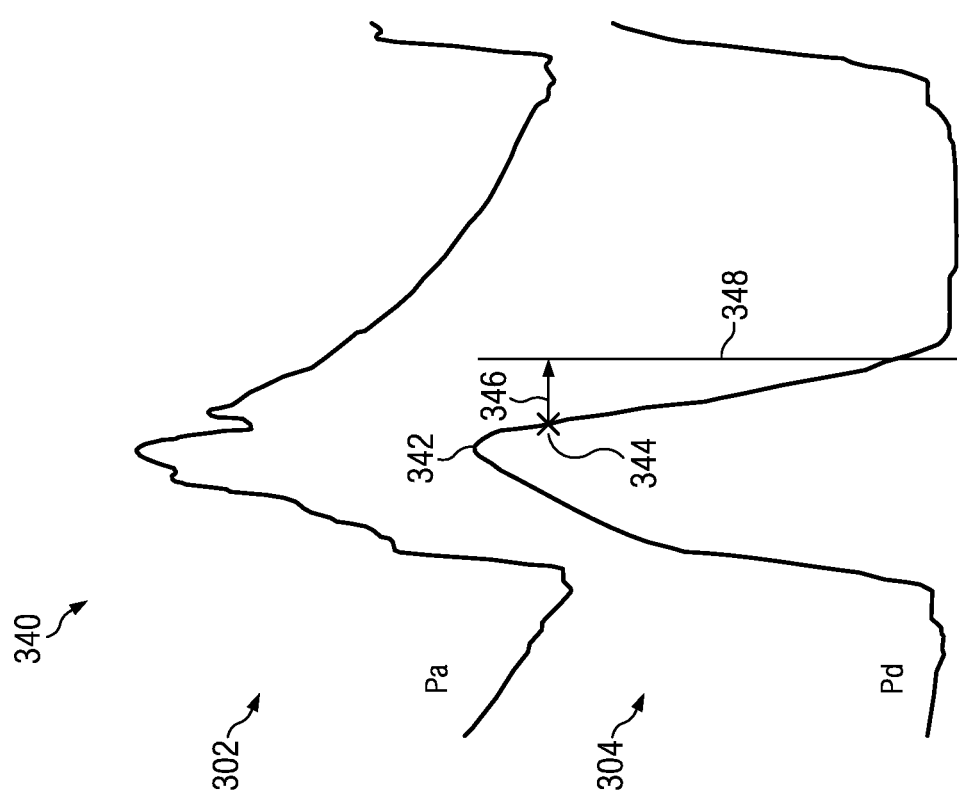
FIG. 20 is a graphical representation of an identification of a starting point of a diagnostic window based on a distal pressure measurement according to another embodiment of the present disclosure.

Referring now to FIG. 20, the starting point of the diagnostic window is determined by identifying a maximum change in pressure and adding a fixed amount of time in some instances. In some particular instances, the maximum change in pressure after a peak distal pressure is utilized as the basis point from which the fixed amount of time is added. As shown in the graphical representation 340 of FIG. 20, after peak pressure 342 the point having a maximum change in pressure (i.e., dP/dt) is identified by point 344. A fixed time period 346 has been added to point 344 to determine the starting point 348 of a diagnostic window. The fixed time period 346 is between about 1 ms and about 500 ms in some instances. In some instances, the fixed time period 346 is between about 25 ms and about 150 ms. In some particular embodiments, the fixed time period 346 is calculated as a percentage of the length of the cardiac cycle of the patient. The percentage of the length of the cardiac cycle utilized for calculating the starting point 348 is between about 0% and about 70% in some instances. In yet other instances, no time is added to the point 344 representative of the maximum change in pressure, such that the point 344 is the starting point 348.

Figure 21:
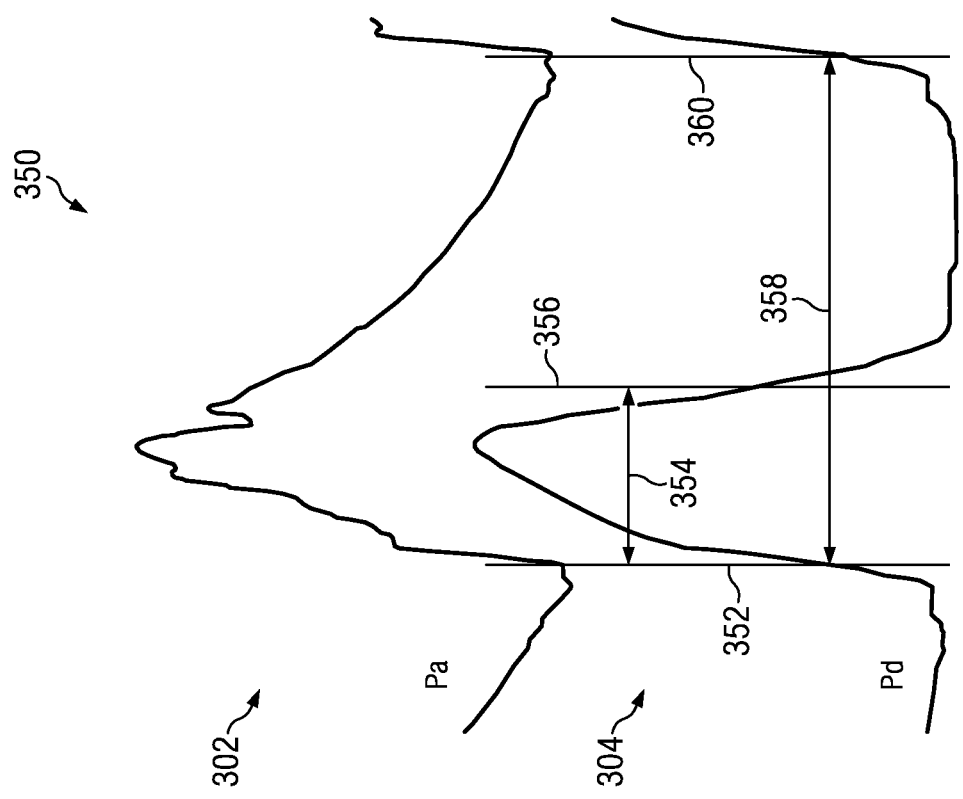
FIG. 21 is a graphical representation of an identification of a starting point of a diagnostic window based on a distal pressure measurement according to another embodiment of the present disclosure.

Referring now to FIG. 21, the starting point of the diagnostic window is determined by identifying the start of a cardiac cycle and adding a fixed amount of time in some instances. As shown in the graphical representation 350 of FIG. 21, a start 352 of the cardiac cycle has been identified and a fixed time period 354 has been added to determine the starting point 356 of a diagnostic window. The fixed time period 354 is between about 150 ms and about 900 ms in some instances. In some instances, the fixed time period 354 is between about 300 ms and about 600 ms. In some particular embodiments, the fixed time period 354 is calculated as a percentage of the length 358 of the cardiac cycle of the patient. As shown in FIG. 21, an end 360 of the cardiac cycle has been identified such that the length 358 of the cardiac cycle extends between the start 352 and the end 360. The percentage of the length 358 of the cardiac cycle utilized for calculating the starting point 356 is between about 25% and about 95% in some instances. In some particular instances, the percentage of the length 358 of the cardiac cycle is between about % and about 75%. In yet other instances, no time is added to the start of the cardiac cycle, such that the start of the cardiac cycle 352 is the starting point 356.

Figure 22:
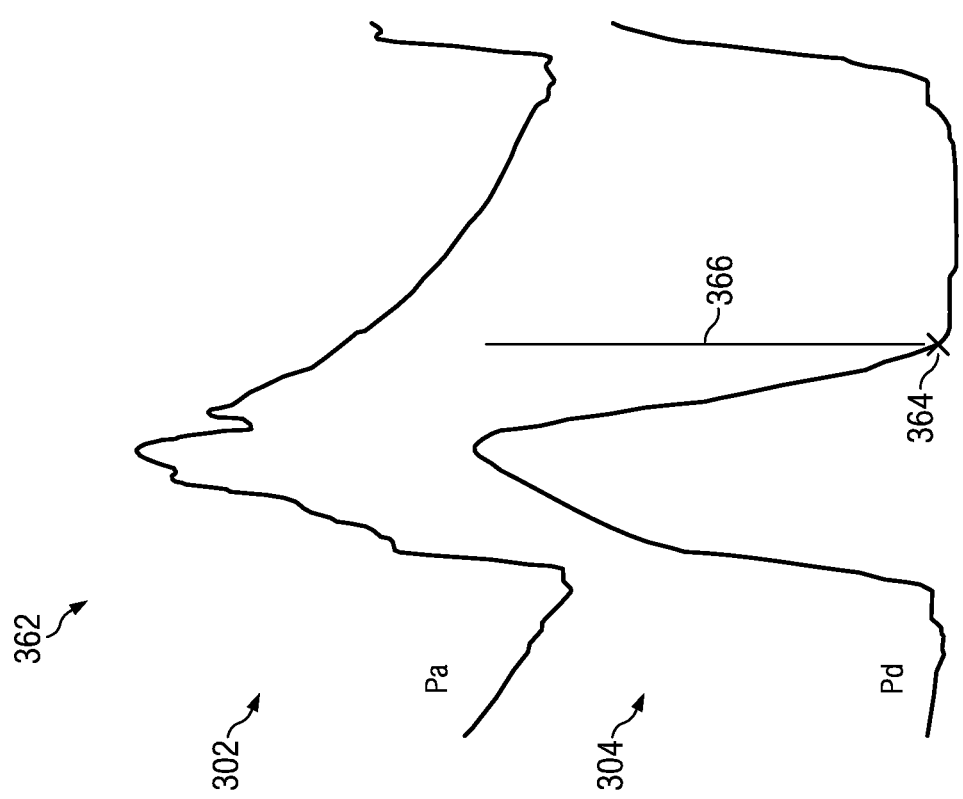
FIG. 22 is a graphical representation of an identification of a starting point of a diagnostic window based on a distal pressure measurement according to another embodiment of the present disclosure.

Referring now to FIG. 22, the starting point of the diagnostic window is determined by identifying a ventricularization point in some instances. As shown in the graphical representation 362 of FIG. 22, a ventricularization point 364 of the cardiac cycle has been identified. In some instances, the ventricularization point 364 is identified based on the change in slope of the distal pressure reading. In the illustrated embodiment, the starting point 366 of the diagnostic window substantially coincides with the ventricularization point 364. In other instances, the starting point 366 is set to be a fixed amount of time before or after the ventricularization point. In that regard, the fixed time period is between about −250 ms and about 400 ms in some instances. In some instances, the fixed time period is between about −50 ms and about 100 ms.

Referring now to FIG. 23, shown therein is a graphical representation 370 illustrating a technique for identifying an ending point of a diagnostic window based on a starting point 372 of the diagnostic window. As shown, the diagnostic window has an ending point 374 that is spaced from the starting point 372 by a fixed amount of time 376. The fixed time period 376 is between about 1 ms and about 700 ms in some instances. In some instances, the fixed time period 376 is between about 200 ms and about 500 ms. In some particular embodiments, the fixed time period 376 is calculated as a percentage of the length of the cardiac cycle of the patient. The percentage of the length of the cardiac cycle utilized for calculating the time period 376 is between about 0% and about 70% in some instances. In some instances, the percentage of the length of the cardiac cycle is between about 25% and about 50%. In other instances, the diagnostic window is a specific point in the cardiac cycle such that time 376 is zero. In that regard, the techniques described for identifying the starting point and/or the ending point of a diagnostic window are suitable for identifying such a diagnostic point in the cardiac cycle for evaluating pressure differential. In some instances, a diagnostic window for a single cardiac cycle is comprised of a plurality of discrete diagnostic points along the single cardiac cycle.

Referring now to FIG. 24, shown therein is a graphical representation 380 illustrating a technique for identifying an ending point of a diagnostic window based on identifying the end of a cardiac cycle according to a proximal pressure measurement, which is an aortic pressure measurement in some instances, and subtracting a fixed amount of time. As shown, an end 382 of the cardiac cycle has been identified and a fixed time period 384 has been subtracted to determine the ending point 386 of a diagnostic window. The fixed time period 384 is between about 1 ms and about 600 ms in some instances. In some particular embodiments, the fixed time period 384 is calculated as a percentage of the length of the cardiac cycle of the patient. The percentage of the length of the cardiac cycle utilized for calculating the time period 384 is between about 0% and about 70% in some instances. In some instances, the percentage of the length of the cardiac cycle is between about 1% and about 25%. In yet other instances, no time is subtracted from the end of the cardiac cycle, such that the end of the cardiac cycle 382 is the ending point 386.

Referring now to FIGS. 25 and 26, shown therein are techniques for identifying an ending point of a diagnostic window based on a distal pressure measurement. Referring more specifically to FIG. 25, shown therein is a graphical representation 390 illustrating a technique for identifying an ending point of a diagnostic window based on identifying the end of a cardiac cycle according to a distal pressure measurement and subtracting a fixed amount of time. As shown, an end 392 of the cardiac cycle has been identified and a fixed time period 394 has been subtracted to determine the ending point 396 of a diagnostic window. The fixed time period 394 is between about 1 ms and about 600 ms. In some instances, the fixed time period 394 is between about 5 ms and about 100 ms. In some particular embodiments, the fixed time period 394 is calculated as a percentage of the length of the cardiac cycle of the patient. The percentage of the length of the cardiac cycle utilized for calculating the time period 394 is between about 0% and about 70%. In some instances, the percentage of the length of the cardiac cycle is between about 1% and about 25%. In yet other instances, no time is subtracted from the end of the cardiac cycle, such that the end of the cardiac cycle 392 is the ending point 396.

Referring to FIG. 26, shown therein is a graphical representation 400 illustrating a technique for identifying an ending of a diagnostic window based on identifying the ventricularization point of a distal pressure measurement. As shown, a ventricularization point 402 of the cardiac cycle has been identified. In some instances, the ventricularization point 402 is identified based on the change in slope of the distal pressure reading. In the illustrated embodiment, an ending point 404 of the diagnostic window substantially coincides with the ventricularization point 402. In other instances, the ending point 404 is set to be a fixed amount of time before or after the ventricularization point. In that regard, the fixed time period is between about −200 ms and about 450 ms. In some instances, the fixed time period is between about −50 ms and about 100 ms.

Figure 27:
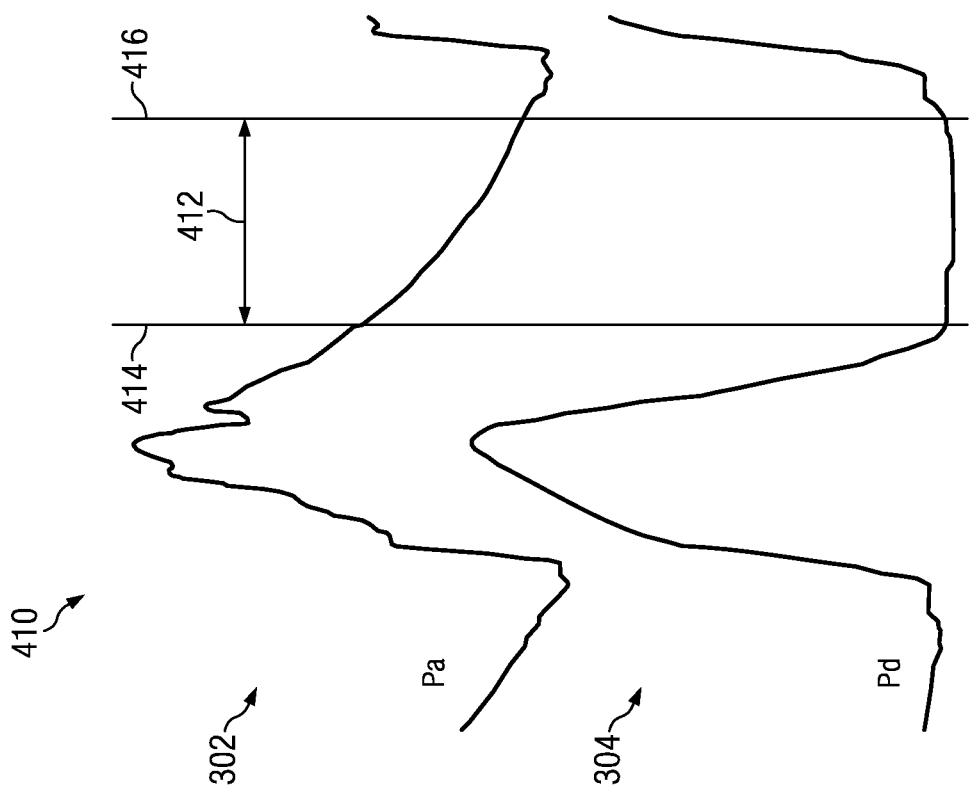
FIG. 27 is a graphical representation of a diagnostic window relative to proximal and distal pressure measurements according to an embodiment of the present disclosure.
Figure 28:
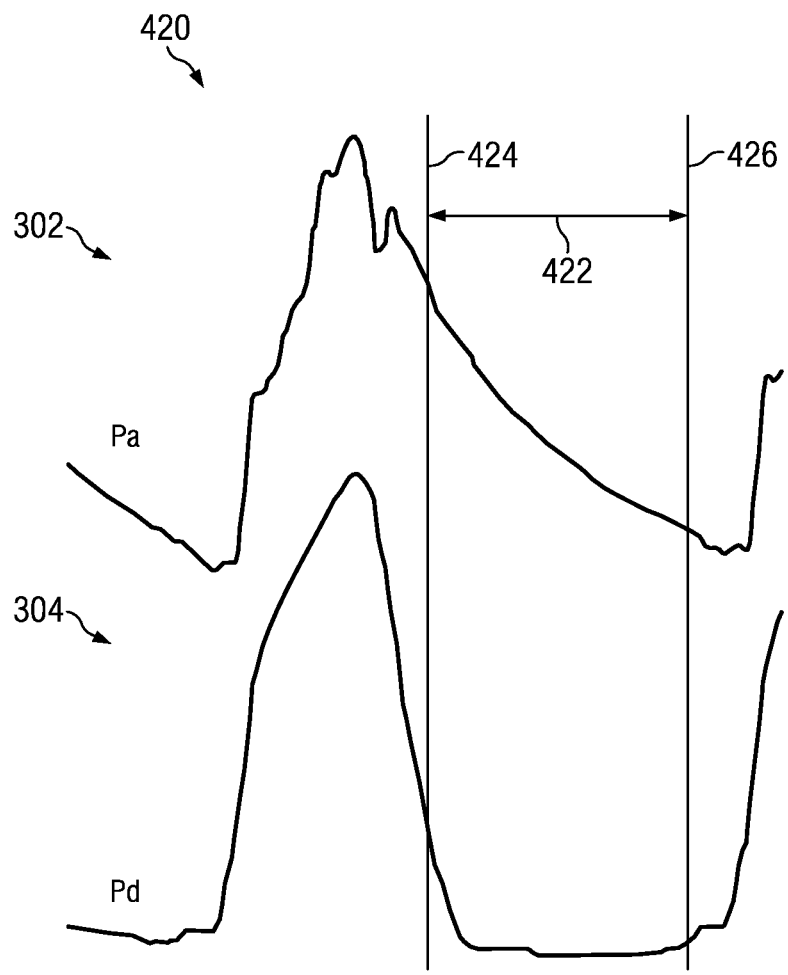
FIG. 28 is a graphical representation of a diagnostic window relative to proximal and distal pressure measurements according to another embodiment of the present disclosure.

Referring now to FIGS. 27 and 28, shown therein are graphical representations of exemplary diagnostic windows relative to proximal and distal pressure measurements. In that regard, FIG. 27 illustrates a diagnostic window that begins shortly after ventricularization, while FIG. 28 illustrates a diagnostic window that begins before ventricularization.

Referring more specifically to FIG. 27, graphical representation 410 shows a diagnostic window 412 that includes a starting point 414 and an ending point 416. In some instances, the starting point 414 is selected using one or more of the techniques described above for identifying a starting point of a diagnostic window. Similarly, in some instances, the ending point 416 is selected using one or more of the techniques described above for identifying an ending point of a diagnostic window. As shown, the diagnostic window 412 begins after the ventricularization point of the distal pressure reading 304 and ends before the end of the cardiac cycle.

Referring now to FIG. 28, graphical representation 420 shows a diagnostic window 422 that includes a starting point 424 and an ending point 426. In some instances, the starting point 424 is selected using one or more of the techniques described above for identifying a starting point of a diagnostic window. Similarly, in some instances, the ending point 426 is selected using one or more of the techniques described above for identifying an ending point of a diagnostic window. As shown, the diagnostic window 422 begins before the ventricularization point of the distal pressure reading 304 and ends before the end of the cardiac cycle such that the ventricularization point is included within the diagnostic window 422.

Figure 29:
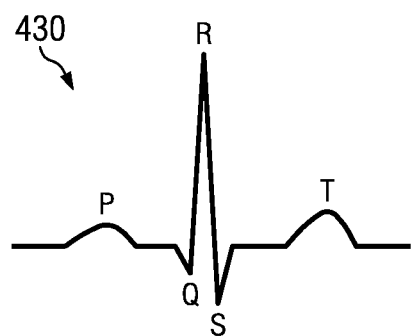
FIG. 29 is graphical representation of an ECG signal according to an embodiment of the present disclosure.

Referring now to FIG. 29, shown therein is graphical representation of an ECG signal annotated with exemplary diagnostic windows according to embodiments of the present disclosure. Generally, at least one identifiable feature of the ECG signal (including without limitation, the start of a P-wave, the peak of a P-wave, the end of a P-wave, a PR interval, a PR segment, the beginning of a QRS complex, the start of an R-wave, the peak of an R-wave, the end of an R-wave, the end of a QRS complex (J-point), an ST segment, the start of a T-wave, the peak of a T-wave, and the end of a T-wave) is utilized to select that starting point and/or ending point of the diagnostic window. For example, in some instances, a diagnostic window is identified using the decline of the T-wave as the starting point and the start of the R-wave as the ending point. In some instances, the starting point and/or ending point of the diagnostic window is determined by adding a fixed amount of time to an identifiable feature of the ECG signal. In that regard, the fixed amount time is a percentage of the cardiac cycle in some instances.

Figure 30:
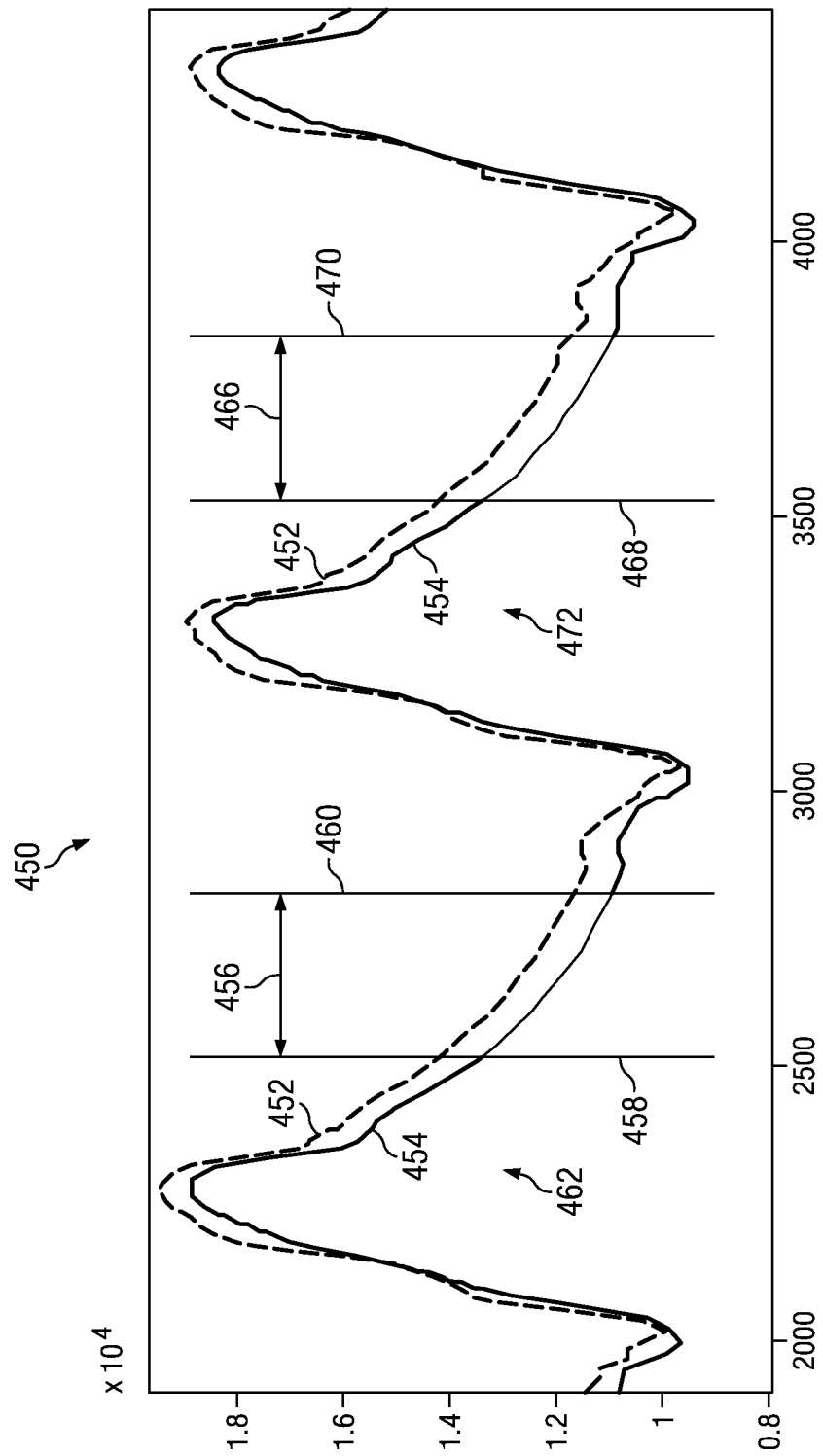
FIG. 30 is a graphical representation of a diagnostic window relative to proximal and distal pressure measurements according to another embodiment of the present disclosure.

Referring now to FIG. 30, shown therein is a graphical representation 450 of a proximal pressure 452 and a distal pressure 454 over a series of cardiac cycles of a patient. In that regard, a diagnostic window 456 has been identified that includes a starting point 458 and an ending point 460 for a cardiac cycle 462. The diagnostic window 456 is defined by the starting point 458 and the ending point 460. In the illustrated embodiment, the starting point 458 is selected to be positioned at a fixed percentage of the total diastole time of the cardiac cycle 462 after a maximum decline in pressure. In some instances, the fixed percentage of the total diastole time added to the point of maximum pressure decline to determine the starting point 458 is between about 10% and about 60%, with some particular embodiments having a percentage between about 20% and about 30%, and with one particular embodiment having a percentage of about 25%. The ending point 560 is selected to be positioned at a fixed percentage of the total diastole time or diastolic window from the beginning of diastole for the cardiac cycle 462. In some instances, the fixed percentage of the total diastole time added to the beginning of diastole to determine the ending point 460 is between about 40% and about 90%, with some particular embodiments having a percentage between about 60% and about 80%, and with one particular embodiment having a percentage of about 70%. In other embodiments, the ending point 560 is selected to be positioned at a fixed percentage of the total diastole time or diastolic window from the end of diastole for the cardiac cycle 462. In some instances, the fixed percentage of the total diastole time subtracted from the end of diastole to determine the ending point 460 is between about 10% and about 60%, with some particular embodiments having a percentage between about 20% and about 40%, and with one particular embodiment having a percentage of about 30%. Accordingly, in the illustrated embodiment, both the starting point 458 and ending point 460 are selected based on a proportion of diastole of the cardiac cycle 462. As a result, diagnostic windows defined using such techniques for multiple cardiac cycles may vary from cardiac cycle to cardiac cycle because the length of diastole may vary from cardiac cycle to cardiac cycle. As shown in FIG. 30, a diagnostic window 466 has been identified that includes a starting point 468 and an ending point 470 for a cardiac cycle 472 that follows cardiac cycle 462. As a result, the diagnostic window 466 will be longer or shorter than the diagnostic window 456, in some instances, because of differences in the length of diastole between cardiac cycle 462 and cardiac cycle 472.

While examples of specific techniques for selecting a suitable diagnostic window have been described above, it is understood that these are exemplary and that other techniques may be utilized. In that regard, it is understood that the diagnostic window is determined using one or more techniques selected from: identifying a feature of a waveform or other data feature and selecting a starting point relative to the identified feature (e.g., before, after, or simultaneous with the feature); identifying a feature of a waveform or other data feature and selecting an ending point relative to the identified feature (e.g., before, after, or simultaneous with the feature); identifying a feature of a waveform or other data feature and selecting a starting point and an ending point relative to the identified feature; identifying a starting point and identifying an ending point based on the starting point; and identifying an ending point and indentifying a starting point based on the ending point.

In some instances, the starting point and/or ending point of a maximum diagnostic window is identified (using one or more of the techniques described above, for example) and then a portion of that maximum diagnostic window is selected for use in evaluating the pressure differential across a stenosis. For example, in some embodiments the portion selected for use is a percentage of the maximum diagnostic window. In some particular embodiments, the portion is between about 5% and about 99% of the maximum diagnostic window. Further, in some instances, the portion selected for use is a centered portion of the maximum diagnostic window. For example, if the maximum diagnostic window was found to extend from 500 ms to 900 ms of a cardiac cycle and a centered portion comprising 50% of the maximum diagnostic window was to be utilized as the selected portion, then the selected portion would correspond with the time from 600 ms to 800 ms of the cardiac cycle. In other instances, the portion selected for use is an off-centered portion of the maximum diagnostic window. For example, if the maximum diagnostic window was found to extend from 500 ms to 900 ms of a cardiac cycle and an off-centered portion comprising 25% of the maximum diagnostic window equally spaced from a mid-point of the maximum window and an ending point of the maximum window was to be utilized as the selected portion, then the selected portion would correspond with the time from 700 ms to 800 ms of the cardiac cycle. In some instances the diagnostic window is selected for each cardiac cycle such that the location and/or size of the diagnostic window may vary from cycle to cycle. In that regard, due to variances in the parameter(s) utilized to select the beginning, end, and/or duration of the diagnostic window from cardiac cycle to cardiac cycle, there is a corresponding variance in the diagnostic window in some instances.

Figure 31:
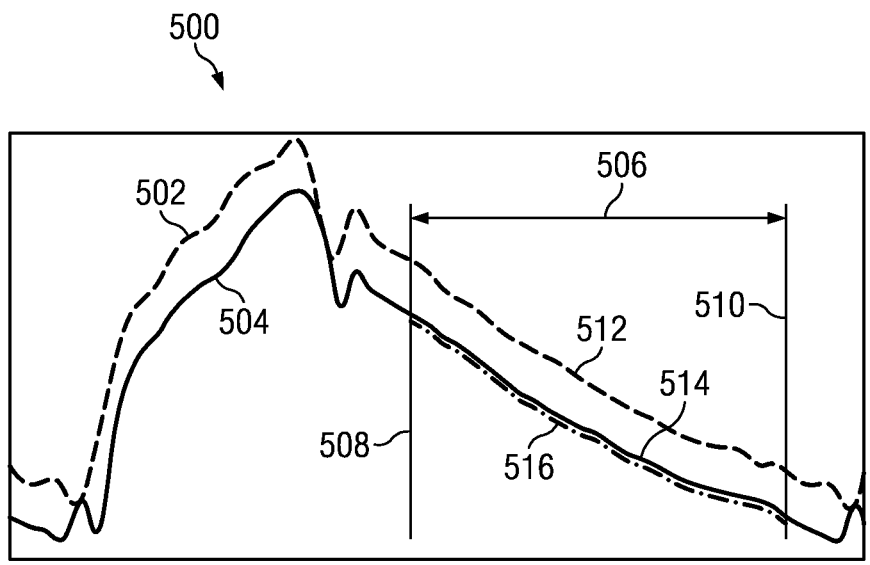
FIG. 31 is a graphical representation of a diagnostic window relative to proximal and distal pressure measurements according to an embodiment of the present disclosure.
Figure 32:
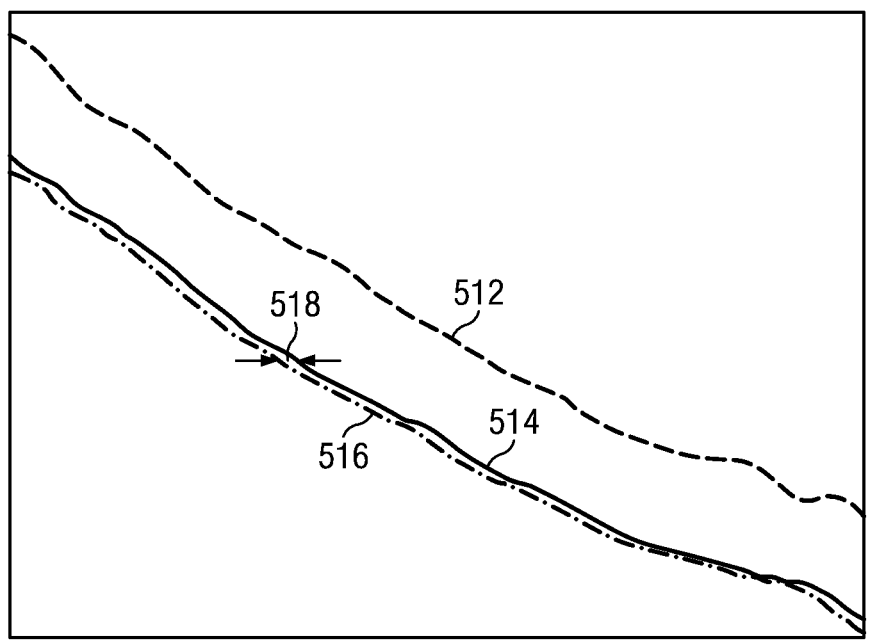
FIG. 32 is a magnified view of a portion of the graphical representation of FIG. 30 illustrating a temporal adjustment of the distal pressure measurement relative to the proximal pressure measurement.

Referring now to FIGS. 31 and 32, shown therein are aspects of calculating a pressure ratio across a stenosis according to an embodiment of the present disclosure. In that regard, FIG. 31 shows a diagnostic window relative to proximal and distal pressure measurements, while FIG. 32 illustrates a temporal adjustment of the distal pressure measurement relative to the proximal pressure measurement.

Referring more specifically to FIG. 31, shown therein is a graphical representation 500 of a proximal pressure 502 and a distal pressure 504 over a cardiac cycle of a patient. In that regard, a diagnostic window 506 has been identified that includes a starting point 508 and an ending point 510. The diagnostic window 506 is suitable for evaluating the severity of a stenosis of the vessel without the need to use a hyperemic agent. In that regard, the diagnostic window 506, starting point 508, and/or ending point 510 are calculated using one or more the techniques described above in some instances. As shown, the proximal pressure 502 includes a portion 512 coinciding with the diagnostic window 506. The distal pressure 504 includes a portion 514 that coincides with the diagnostic window 506.

Referring now to FIG. 32, for a variety of reasons, the proximal pressure 502 and distal pressure 504 are not temporally aligned in some instances. For example, during data acquisition, there will often be a delay between the distal pressure measurement signals and the proximal pressure measurement signals due to hardware signal handling differences between the instrument(s) utilized to obtain the measurements. In that regard, the differences can come from physical sources (such as cable length and/or varying electronics) and/or can be due to signal processing differences (such as filtering techniques). In some embodiments, the proximal pressure measurement signal is acquired by and routed through a hemodynamic monitoring system and may take significantly longer to reach the processing hardware or computing device compared to the distal pressure measurement signal that is sent more directly to the processing hardware or computing device. The resulting delay is between about 5 ms and about 150 ms in some instances. Because individual cardiac cycles may last between about 500 ms and about 1000 ms and the diagnostic window may be a small percentage of the total length of the cardiac cycle, longer delays between the proximal and distal pressure measurement signals can have a significant impact on alignment of the pressure data for calculating a pressure differential for a desired diastolic window of a cardiac cycle.

As a result, in some instances, it is necessary to shift one of the proximal and distal pressures relative to the other of the distal and proximal pressures in order to temporally align the pressure measurements. In the illustrated embodiment of FIG. 32, a portion of the distal pressure 504 has been shifted to be temporally aligned with the portion 512 of the proximal pressure 502 coinciding with the diagnostic window 506. In that regard, a portion 516 of the distal pressure 504 that has been shifted, as indicated by arrow 518, to be aligned with the portion 512 of the proximal pressure 502. While FIG. 32 illustrates a shift of only a portion of the distal pressure 504 into alignment with the proximal pressure, in other embodiments all or substantially all of the proximal and distal pressures are aligned before the portions corresponding to a selected diagnostic window are identified.

Alignment of all or portion(s) of the proximal and distal pressures is accomplished using a hardware approach in some instances. For example, one or more hardware components are positioned within the communication path of the proximal pressure measurement, the distal pressure measurement, and/or both to provide any necessary delays to temporally align the received pressure signals. In other instances, alignment of all or portion(s) of the proximal and distal pressures is accomplished using a software approach. For example, a cross-correlation function or matching technique is utilized to align the cardiac cycles in some embodiments. In other embodiments, the alignment is based on a particular identifiable feature of the cardiac cycle, such as an ECG R-wave or a pressure peak. Additionally, in some embodiments alignment is performed by a software user where adjustments are made to the delay time of at least one of the proximal and distal pressures until the cardiac cycles are visually aligned to the user. A further technique for aligning the signals is to apply a synchronized timestamp at the point of signal acquisition. Further, in some instances combinations of one or more of hardware, software, user, and/or time-stamping approaches are utilized to align the signals.

Regardless of the manner of implementation, several approaches are available for the aligning the proximal and distal pressure measurement signals. In some instances, each individual distal pressure measurement cardiac cycle is individually shifted to match the corresponding proximal pressure measurement cardiac cycle. In other instances, an average shift for a particular procedure is calculated at the beginning of the procedure and all subsequent cardiac cycles during the procedure are shifted by that amount. This technique requires little processing power for implementation after the initial shift is determined, but can still provide a relatively accurate alignment of the signals over the course of a procedure because the majority of the signal delay is due to fixed sources that do not change from patient to patient or within the procedure. In yet other instances, a new average shift is calculated each time that the proximal and distal pressure signals are normalized to one another during a procedure. In that regard, one or more times during a procedure the sensing element utilized for monitoring pressure distal of the stenosis is positioned adjacent the sensing element utilized for monitoring pressure proximal of the stenosis such that both sensing elements should have the same pressure reading. If there is a difference between the pressure readings, then the proximal and distal pressure signals are normalized to one another. As a result, the subsequently obtained proximal and distal pressure measurements are more consistent with each other and, therefore, the resulting pressure ratio calculations are more accurate.

With the proximal and distal pressure measurements aligned, the pressure ratio for the diagnostic window 506 is calculated. In some instances, the pressure ratio is calculated using average values for the proximal and distal pressure measurements across the diagnostic window. The pressure ratio calculations of the present disclosure are performed for a single cardiac cycle, in some instances. In other instances, the pressure ratio calculations are performed for multiple cardiac cycles. In that regard, accuracy of the pressure ratio can be improved by performing the pressure ratio calculations over multiple cardiac cycles and averaging the values and/or using an analysis technique to identify one or more of the calculated values that is believed to be most and/or least accurate.

Figure 33:
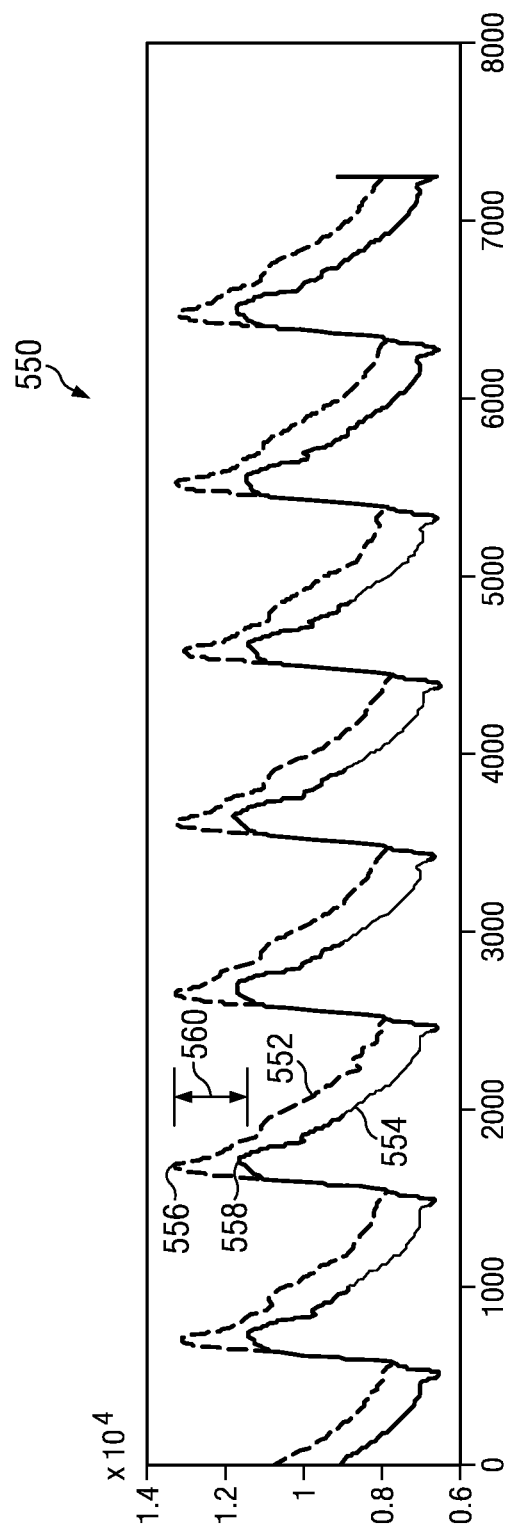
FIG. 33 is a graphical representation of proximal and distal pressure measurements within a vessel according to an embodiment of the present disclosure.

Referring now to FIG. 33, shown therein is a graphical representation 550 of proximal and distal pressure measurements within a vessel according to an embodiment of the present disclosure. In that regard, the graphical representation 550 includes a proximal pressure measurement waveform 552 and a distal pressure measurement waveform 554. Generally, the proximal pressure measurement waveform 552 is representative of pressure measurements obtained proximal of a lesion or region of interest of a vessel and the distal pressure measurement waveform 554 is representative of pressure measurements obtained distal of the lesion or region of interest of the vessel. The proximal pressure measurement waveform 552 has a peak pressure at point 556 and the distal pressure measurement waveform 554 has a peak pressure at point 558. In that regard, the peak pressures occur during systole of each heartbeat cycle at or around the systolic wave-free period. In the illustrated embodiment, there is a difference 560 between the peak proximal pressure 556 and the peak distal pressure 558. In some embodiments, the difference 560 is calculated as the peak proximal pressure 556 minus the peak distal pressure 558. In other embodiments, the difference is calculated as the peak distal pressure 558 minus the peak proximal pressure 556.

In some instances, this difference between the peak pressures is taken into account when calculating the ratio of the distal pressure to the proximal pressure during a selected diagnostic window using one or more of the techniques discussed above. In that regard, the difference 560 between the peak proximal pressure 556 and the peak distal pressure 558 is determined and then compensated for in making the pressure ratio calculation. For example, in some embodiments, the difference 560 between the peak pressures is added to the distal pressure measurement during the diagnostic window such that the pressure ratio during the diagnostic window is calculated as $(P_{Distal}+\text{Peak Pressure Difference})/P_{proximal}$. In one such embodiment, the difference is calculated as the peak proximal pressure 556 minus the peak distal pressure 558. In other embodiments, the difference 560 between the peak pressures is subtracted from the distal pressure measurement during the diagnostic window such that the pressure ratio during the diagnostic window is calculated as $(P_{Distal}-\text{Peak Pressure Difference})/P_{proximal}$. In one such embodiment, the difference is calculated as the peak distal pressure 558 minus the peak proximal pressure 556.

In other instances, a ratio of the peak proximal and distal pressures is calculated. The ratio of peak pressures can then be used as a scaling factor to adjust the pressure ratio calculations made during the diagnostic window. For example, in one embodiment, the peak pressure ratio is calculated by dividing the peak proximal pressure by the peak distal pressure. Then the standard pressure ratio calculated across a diagnostic window using one or more of the techniques described above can be scaled by multiplying the standard pressure ratio calculation by the ratio of peak pressures. In this manner, the ratio of peak pressures can be used as a scaling factor for calculating the pressure ratio during the diagnostic window. Using either the peak pressure difference or the peak pressure ratio, differences in pressure present during systole can be compensated for when calculating the pressure ratio during the diagnostic window used to evaluate the vessel. This compensation can be particularly useful in situations where the diagnostic window is selected to be during a wave-free period in diastole following shortly after systole.

Figure 34:
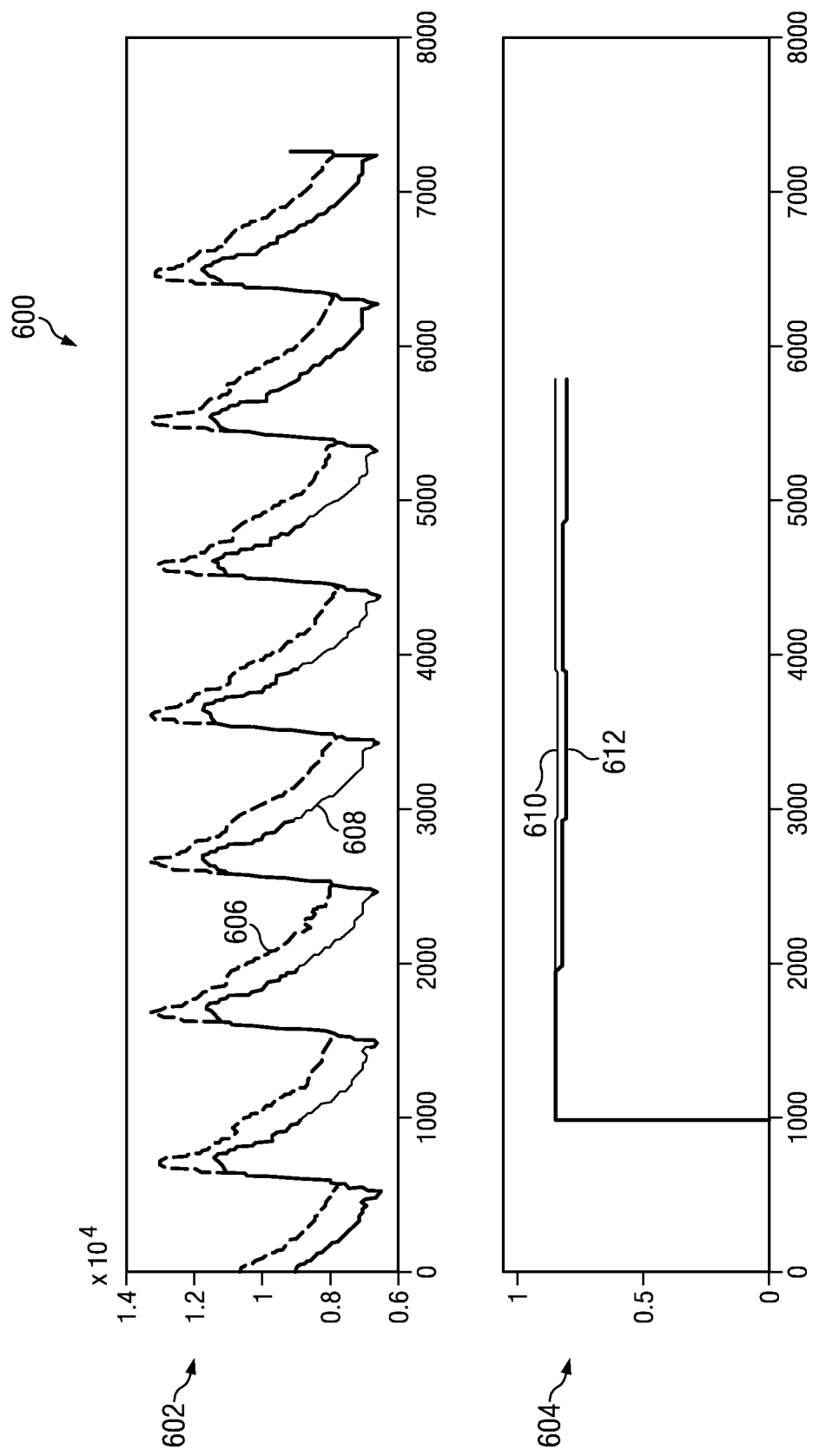
FIG. 34 is a pair of graphical representations, where the top graphical representation illustrates proximal and distal pressure measurements within a vessel and the bottom graphical representation illustrates a ratio of the proximal and distal pressure measurements and a fit between the proximal pressure waveform and the distal pressure waveform according to an embodiment of the present disclosure.
Figure 35:
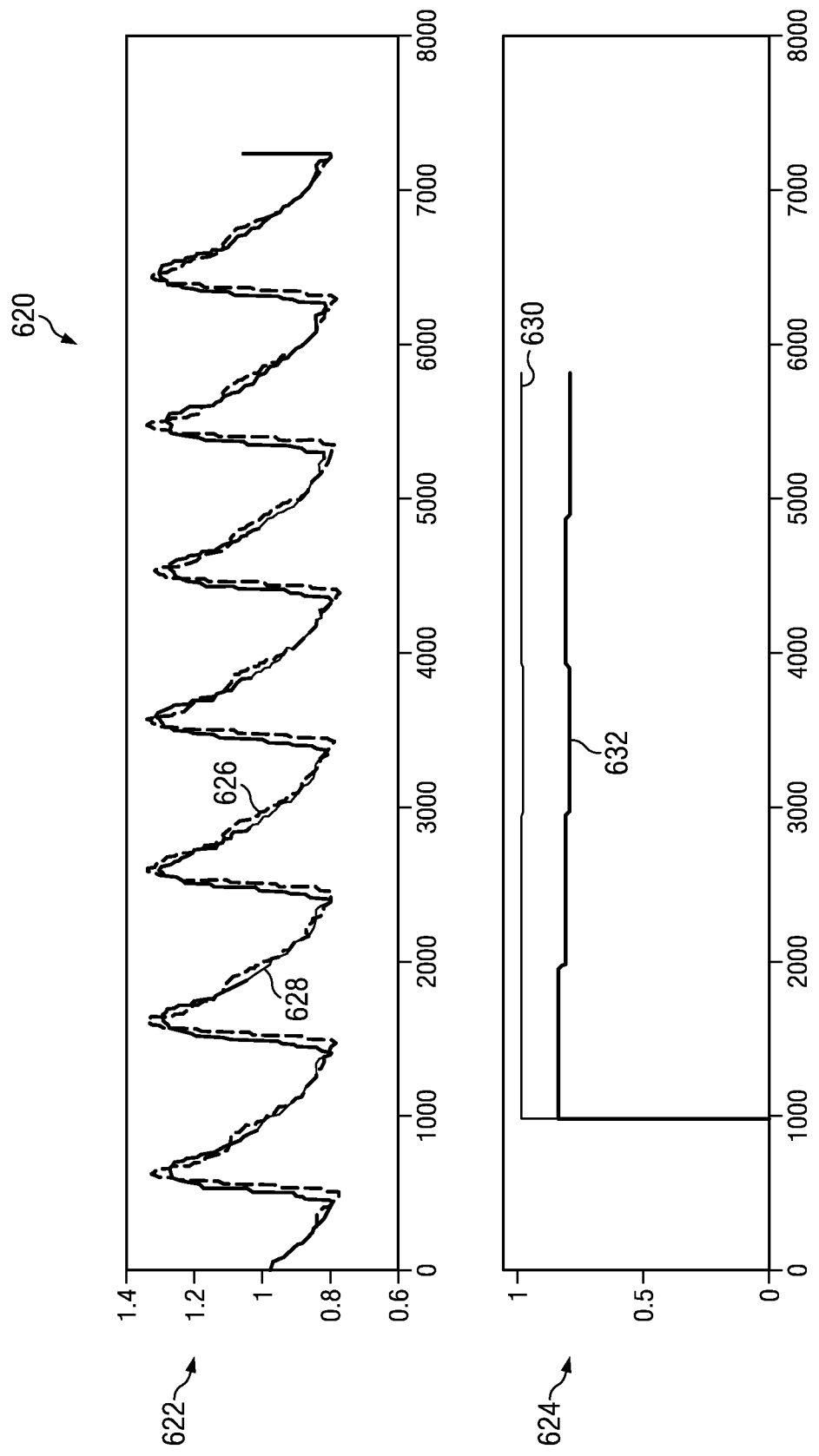
FIG. 35 is a pair of graphical representations similar to that of FIG. 33, but where the distal pressure measurement waveform of the top graphical representation has been shifted relative the distal pressure waveform of FIG. 33 and the bottom graphical representation illustrates the corresponding ratio of the proximal and distal pressure measurements and the fit between the proximal pressure waveform and the distal pressure waveform based on the shifted distal pressure measurement waveform.

Referring now to FIGS. 34 and 35, shown therein are aspects of a technique for evaluating a vessel according to another embodiment of the present disclosure. In that regard, the technique described below with respect to FIGS. 34 and 35 may be implemented using any of the diagnostic windows and associated techniques discussed above for evaluating a vessel using a pressure ratio across a lesion, stenosis, or region of interest. However, as will be discussed in greater detail, the technique associated with FIGS. 34 and 35 is not dependent upon the accuracy of the pressure measurements to evaluate the stenosis. Accordingly, concerns about pressure transducer drift during a procedure are largely reduced or eliminated by this technique. Further, the need to repeatedly calibrate or normalize the distal pressure measurement device to the proximal pressure measurement device during a procedure is likewise reduced or eliminated.

Referring initially to FIG. 34, shown therein is a graphical representation 600 illustrating aspects of the technique for evaluating a vessel according to the current embodiment of the present disclosure. As shown, the graphical representation 600 includes a graph 602 and a graph 604. Graph 602 illustrates a proximal pressure waveform 606 and a distal pressure waveform 608 of a patient over time. Graph 604, in turn, illustrates corresponding calculations based on those waveforms 606 and 608. In that regard, plot 610 is representative of a pressure ratio of the distal pressure waveform 608 relative to the proximal pressure waveform 606 over time, which in some embodiments is during a wave free period of the heartbeat cycle. Plot 610 is representative of the pressure ratio calculation used in some of the vessel evaluation techniques described above. Plot 612 is representative of a slope comparison between the distal pressure waveform 608 and the proximal pressure waveform 606. In that regard, the slope of the distal pressure waveform 608 is compared to the slope of the proximal pressure waveform 606 to provide an indication of the severity of a lesion or stenosis. In some instances, a best fit regression slope is utilized. In that regard, one or more of polynomial fitting, multiple line regression, estimation of the slope from points at either end of the waveforms, and/or other suitable fitting techniques are utilized. Further, the fitting may be performed over a single heartbeat or over multiple heartbeat cycles. When the slope of the distal pressure waveform 608 is equal to the slope of the proximal pressure waveform 606, then the polyfit regression slope (i.e., a slope obtained through polynomial curve fitting) will be equal to 1.0, which is indicative of no lesion or stenosis. On the other hand, as the slope of the distal pressure waveform 608 diverges from the slope of the proximal pressure waveform 606, then the polyfit regression slope move towards 0.0, which is indicative of a severe lesion or stenosis (e.g., total occlusion or severe blockage). Accordingly, the severity of the lesion or stenosis can be evaluated based on the polyfit regression slope. More specifically, the closer the polyfit regression slope is to 1.0 the less severe the lesion/stenosis and the closer the polyfit regression slope is to 0.0 the more severe the lesion/stenosis. Similar to the 0.80 cutoff for pressure ratios discussed above, a predetermined threshold value can be utilized for the regression slope comparison. For example, in some instances, the predetermined threshold value is between about 0.70 and about 0.90, with some particular embodiments using a threshold value of 0.75, 0.80, 0.85, or otherwise. In other instances, the predetermined threshold value is less than 0.70 or greater than 0.90.

As noted above, this slope-based technique is not dependent upon the accuracy of the pressure measurements to evaluate the stenosis. In that regard, FIG. 35 illustrates this point. Shown therein is a graphical representation 620 that includes a graph 622 and a graph 624. Graph 622 illustrates a proximal pressure waveform 626 and a distal pressure waveform 628 of a patient over time. In that regard, proximal pressure waveform 626 is the same as proximal pressure waveform 606 of FIG. 34 and distal pressure waveform 628 is substantially the same as distal pressure waveform 608 of FIG. 34, but to illustrate the effects of transducer drift the distal pressure waveform 628 has been increased by a constant value of 10 mmHg compared to distal pressure waveform 608. Graph 624 illustrates corresponding calculations based on those waveforms 626 and 628. In that regard, plot 630 is representative of a pressure ratio of the distal pressure waveform 628 relative to the proximal pressure waveform 626 over time. Notably, the values of plot 630 are substantially increased relative to the values of plot 610 of FIG. 34. This illustrates one of the potential problems of an inaccurate and/or non-normalized distal pressure measurement in the context of the pressure ratio calculation. On the other hand, plot 632 is representative of a slope comparison between the distal pressure waveform 628 and the proximal pressure waveform 626. As shown, plot 632 substantially matches plot 612 of FIG. 34. This is because plots 612 and 632 are based upon the shape of the proximal and distal waveforms, which are the same between FIGS. 34 and 35. In that regard, the distal pressure waveform 628 has the same shape as distal pressure waveform 608, it has simply been shifted upward by a value of 10 mmHg. As a result, plots 612 and 632 based on the slopes of the waveforms are pressure-value independent and, therefore, drift independent. It is understood that this waveform shape and/or waveform slope based technique can be implemented using the waveforms from any of the diagnostic windows discussed above.

One advantage of the techniques of the present disclosure for identifying diagnostic windows and evaluating pressure differentials is the concept of "beat matching". In that regard, the proximal and distal waveforms for the same cardiac cycle are analyzed together with no averaging or individual calculations that span more than a single cardiac cycle. As a result, interruptions in the cardiac cycle (such as ectopic heartbeats) equally affect the proximal and distal recordings. As a result, these interruptions that can be detrimental to current FFR techniques have minor effect on the techniques of the present disclosure. Further, in some embodiments of the present disclosure, the effect of interruptions in the cardiac cycle and/or other irregularities in the data is further minimized and/or mitigated by monitoring the pressure differential calculations to detect these anomalies and automatically exclude the impacted cardiac cycles.

In one particular embodiment, pressure ratio is calculated on two sequential cardiac cycles and the individual pressure ratio values are averaged. The pressure ratio of a third cycle is then calculated. The average value of the pressure ratios is compared to the average pressure ratio using three cycles. If the difference between the averages is below a predetermined threshold value, then the calculated value is considered to be stable and no further calculations are performed. For example, if a threshold value of 0.001 is used and adding an additional cardiac cycle changes the average pressure ratio value by less than 0.001, then the calculation is complete. However, if the difference between the averages is above the predetermined threshold value, then the pressure ratio for a fourth cycle is calculated and a comparison to the threshold value is performed. This process is repeated iteratively until the difference between the averages of cardiac cycle N and cardiac cycle N+1 is below the predetermined threshold value. As the pressure ratio value is typically expressed to two decimal places of precision (such as 0.80), the threshold value for completing the analysis is typically selected to be small enough that adding a subsequent cardiac cycle will not change the pressure differential value. For example, in some instances the threshold value is selected to be between about 0.0001 and about 0.05.

In some instances, the level of confidence calculation has different thresholds depending on the degree of stenosis and/or an initial calculated pressure ratio. In that regard, pressure ratio analysis of a stenosis is typically based around a cutoff value(s) for making decisions as to what type of therapy, if any, to administer. Accordingly, in some instances, it is desirable to be more accurate around these cutoff points. In other words, where the calculated pressure ratio values are close to a cut-off, a higher degree of confidence is required. For example, if the cutoff for a treatment decision is at 0.80 and the initial calculated pressure ratio measurement is between about 0.75 and about 0.85, then a higher degree of confidence is needed than if the initial calculated pressure ratio measurement is 0.40, which is far from the 0.80 cutoff point. Accordingly, in some instances the threshold value is at least partially determined by the initial calculated pressure ratio measurement. In some instances, the level of confidence or stability of the calculated pressure ratio is visually indicated to user via a software interface. For example, the color of the calculated pressure ratio may change as the confidence level increases (e.g., fading from a darker color to a brighter color), the user interface may include a confidence scale with a corresponding marker displayed for the particular calculation (e.g., a sliding scale or a bullseye where an indicator of confidence moves closer to the bullseye as confidence increases), the pressure ratio value may transition from a fuzzy or unclear display to a sharp, clear display as confidence increase, and/or other suitable indicators for visually representing the amount of confidence or perceived preciseness of a measurement.

Because pressure ratio can be calculated based on a single cardiac cycle in accordance with the present disclosure, a real-time or live pressure ratio calculation can made while the distal pressure measuring device is moved through the vessel. Accordingly, in some instances the system includes at least two modes: a single-cardiac-cycle mode that facilitates pressure ratio calculations while moving the distal pressure measuring device through the vessel and a multi-cardiac-cycle mode that provides a more precise pressure ratio calculation at a discrete location. In one embodiment of such a system, the software user interface is configured to provide the live pressure ratio value until the distal pressure measuring device is moved to the desired location and a measurement button is selected and/or some other actuation step is taken to trigger the multi-cardiac-cycle mode calculation.

Persons skilled in the art will also recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for evaluating a stenosis of a vessel of a patient, the system comprising:
   a processing unit configured for communication with a pressure-sensing guide wire and a pressure-sensing instrument, wherein the processing unit is configured to:
   receive proximal pressure measurements for a plurality of cardiac cycles of the patient from the pressure-sensing instrument;
   receive distal pressure measurements for the plurality of cardiac cycles from the pressure-sensing guide wire, wherein the proximal pressure measurements and the distal pressure measurements are obtained without application of a hyperemic agent to the patient;
   perform a pressure ratio calculation based on the proximal pressure measurements and the distal pressure measurements, wherein the pressure ratio calculation results in a plurality of pressure ratios corresponding to the plurality of cardiac cycles;
   monitor the pressure ratio calculation to detect an anomaly impacting a cardiac cycle of the plurality of cardiac cycles;
   automatically exclude a pressure ratio of the plurality of pressure ratios corresponding to the impacted cardiac cycle; and
   output, to a display in communication with the processing unit, a pressure ratio indicator based on the plurality of pressure ratios other than the excluded pressure ratio.

2. The system of claim 1, wherein the pressure ratio indicator comprises a plot based on the plurality of pressure ratios.

3. The system of claim 1, wherein the anomaly comprises an interruption in the plurality of cardiac cycles.

4. The system of claim 1, wherein the anomaly comprises an irregularity in at least one of the proximal pressure measurements or the distal pressure measurements.

5. The system of claim 1, wherein the pressure ratio calculation results in a respective pressure ratio for each of the plurality of cardiac cycles.

6. The system of claim 5, wherein the pressure ratio indicator is based on an average of the respective pressure ratios for each of the plurality of cardiac cycles.

7. The system of claim 6, wherein the processing unit is further configured to calculate a difference between the average for cardiac cycles 1 to n and the average for cardiac cycles 1 to n+1.

8. The system of claim 7, wherein the processing unit is configured to output the pressure ratio indicator only when the difference is below a threshold value.

9. The system of claim 8, wherein the threshold value is between about and about 0.05.

10. The system of claim 1, further comprising the pressure-sensing guide wire.

11. The system of claim 1, further comprising the pressure-sensing instrument.

12. The system of claim 11, wherein the pressure-sensing instrument comprises a pressure-sensing catheter.

13. The system of claim 11, wherein the pressure-sensing instrument comprises a further pressure-sensing guide wire.

* * * * *